(12) United States Patent
Denhardt et al.

(10) Patent No.: US 6,414,219 B1
(45) Date of Patent: Jul. 2, 2002

(54) OSTEOPONTIN KNOCK-OUT MOUSE AND METHODS OF USE THEREOF

(75) Inventors: David T. Denhardt, Bridgewater; Susan R. Rittling, Kingston, both of NJ (US); Masaki Noda, Tokyo (JP); Aaron J. Kowalski, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/340,484

(22) Filed: Jun. 30, 1999

Related U.S. Application Data

(60) Provisional application No. 60/091,200, filed on Jun. 30, 1998.

(51) Int. Cl.$^7$ .................... A01K 67/027; G01N 33/00; C12N 15/00; C12N 15/63; C07H 21/04
(52) U.S. Cl. .................... 800/18; 800/3; 800/25; 536/23.5; 435/320.1; 435/325; 435/455
(58) Field of Search .................... 800/3, 18, 25; 536/23.1, 23.5; 424/93.1, 93.21; 435/320.1, 325, 455

(56) References Cited

PUBLICATIONS

Ewan R. Cameron. Recent advances in transgenic technology. Molecular Biotechnology. 7/3: 253–265, 1997.*
Liaw et al. Altered wound healing in mice lacking a functional osteopontin gene (spp1). The Journal of Clinical Investigation. 101/7: 1468–1478. 1998, 1997.*
Moens et al, 1993, Development, 119: 485–499.*
Moreadith et al, 1997, J. Mol. Med., 75: 208–216.*
Giachelli et al., 1995, Molecular and cellular biology of osteopontin, TMC 5:88–95.
Feng et al., 1995, Osteopontin may facilitate metastasis by protecting cells . . . , Clin. Exp. Metastasis 13:453–462.
Zheng et al., 1995, Vitronectin is not essential for normal mammalian development and fertility, PNAS 92:12426–12430.
Yamate et al., 1997, Osteopontin expression by osteoclast and osteoblast progenitors . . . , Endocrinology 138:3047–3055.
McKee et al., 1997. Hard tissue development, structure and composition in transgenic mice lacking osteopontin, Mole. Biol. of the Cell 8: suppl. Abstract #422.
Rittling et al., 1997, Skeletal structure is normal while in vitro osteoclastogenesis is enhanced in mice deficient for osteopontin, JBMR 12:suppl,Abstract #180.
Rollo et al., 1996, Osteopontin inhibits nitric oxide production and cytotoxicity by activated RAW264.7 macrophages, J. Leuko. Biol. 60:397–404.
Senger et al., 1996, Stimulation of endothelial cell migration . . . , Am. J. Pathology 149:293–305.
Chen et al., 1993, Developmental expression of osteopontin (OPN) mRNA in rat tissues matrix 13:113–1123.
McKee and Nanci, 1996, Osteopontin: an interfacial extracellular matrix protein in mineralized tissues, Connective Tissue Research 35:197–205.
Boskey et al., 1993, Osteopontin–hydroxyapatite interactions in vitro, Bone and Mineral, 22:147–159.
Liaw, et al. April 1998. Altered wound Healing in Mice Lacking a Functional Osteopontin Gene (spp1) Dept. of Cell Biology. The Journal of Clinical Investigation. 101, 7:1468–1478.
Abstract–#1409, Law and Hogan, Osteopontin is not Essential for Mouse Embryonic Development. Dept. of Cell Biology. Supplement to Mol. Biol. of Cell (1996) 7:234A.
Abstract–#54, Law and Hogan, Targeted Mutation of the Mouse osteopontin gene. Dept. Cell Biology Dev. Biology. (1996) 175:388.

* cited by examiner

Primary Examiner—Deborah J. R. Clark
Assistant Examiner—Peter Paras, Jr.
(74) Attorney, Agent, or Firm—Dann, Dorfman, Herrell and Skillman

(57) ABSTRACT

A transgenic non-human animal with alterations in the osteopontin gene is prepared by introduction of a gene encoding an altered osteopontin protein into a host non-human animal. Methods for using transgenic mice so generated to screen for agents that effect osteopontin's cellular modulating activity are also provided.

9 Claims, 16 Drawing Sheets

(9 of 16 Drawing Sheet(s) Filed in Color)

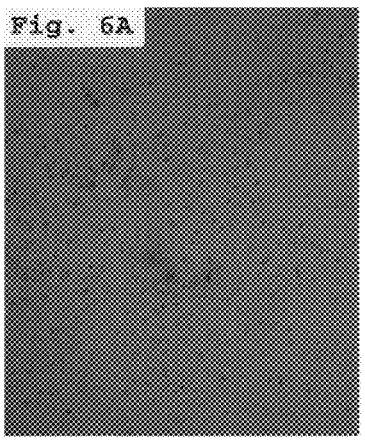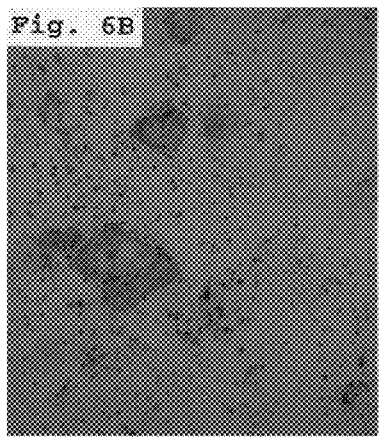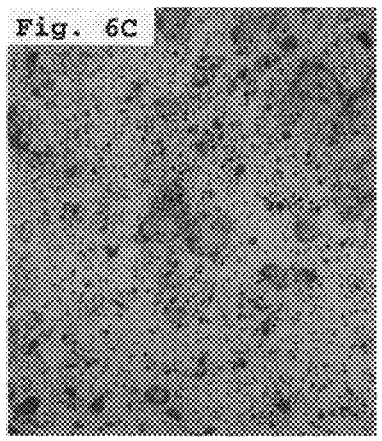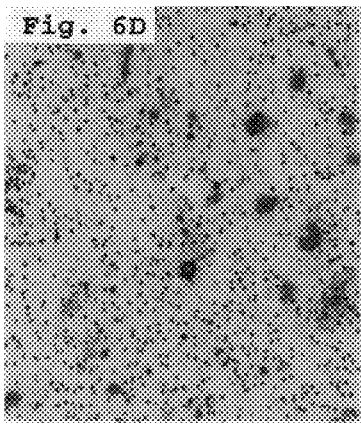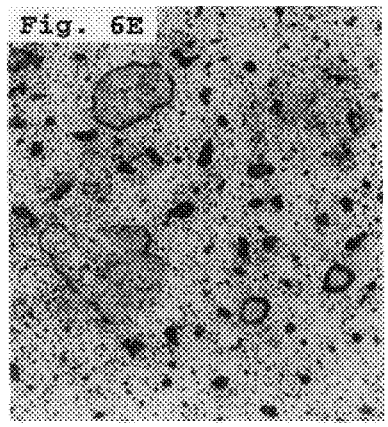

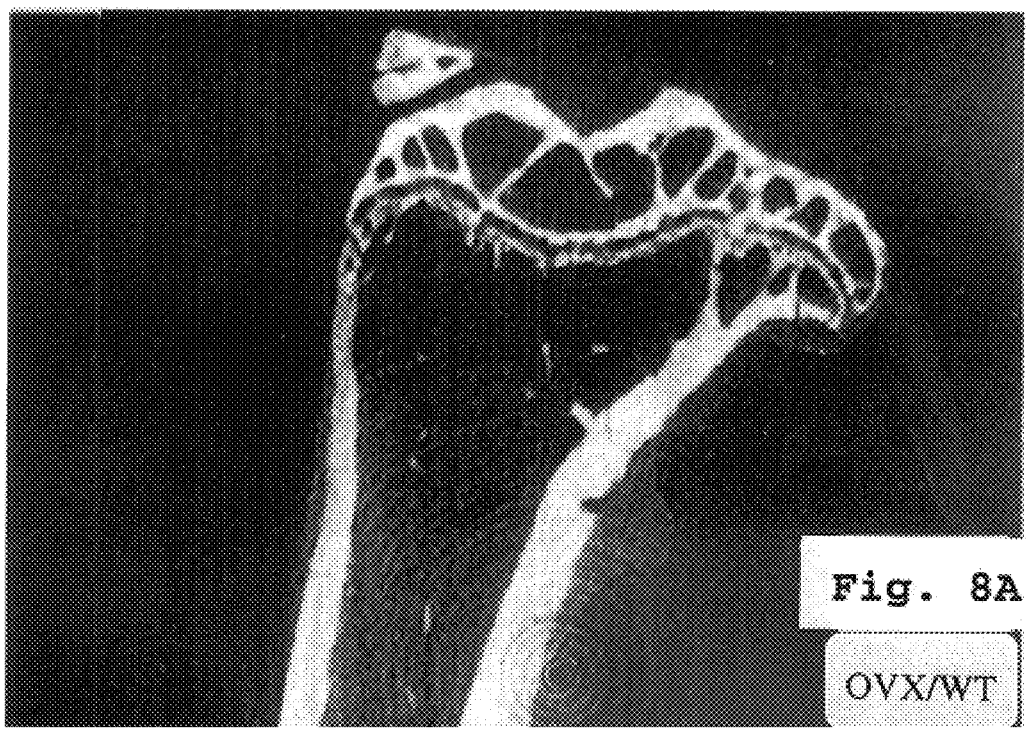
Fig. 8A OVX/WT
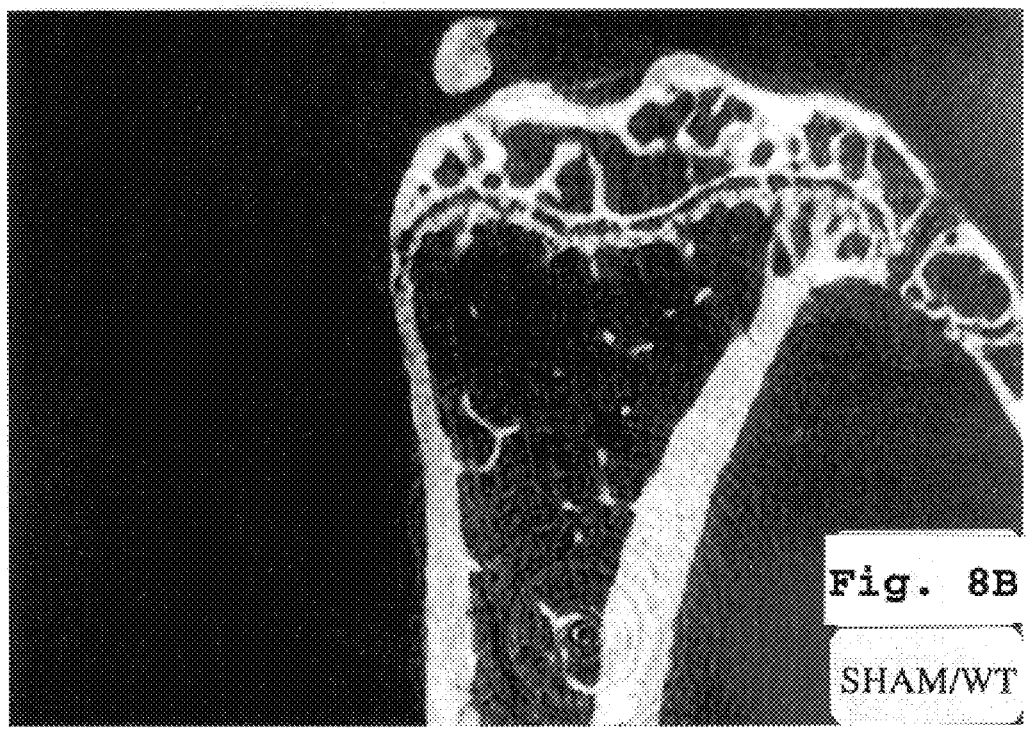
Fig. 8B SHAM/WT

OVX/KO

SHAM/KO

OVX/WT

SHAM/WT

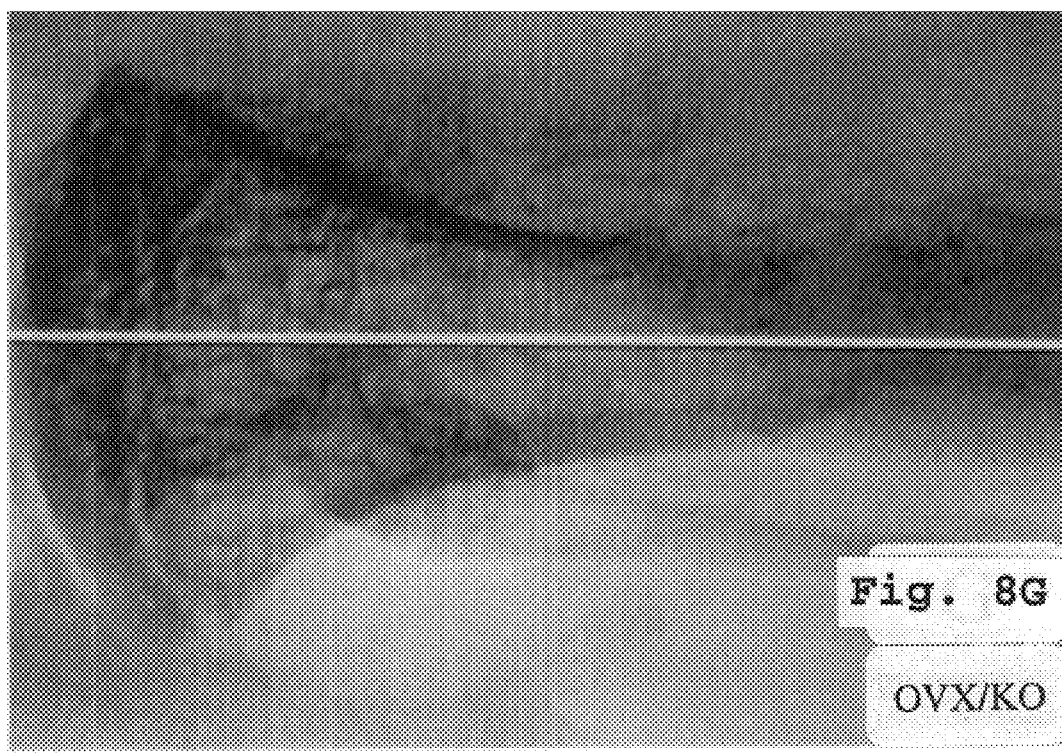
Fig. 8G OVX/KO
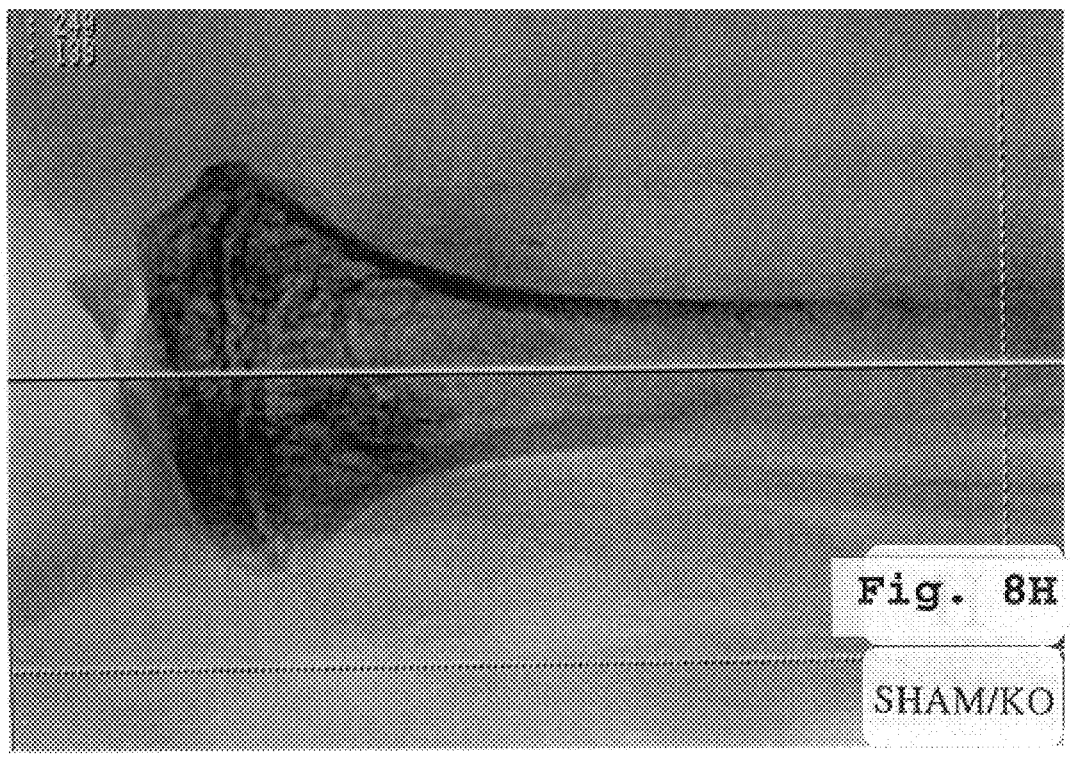
Fig. 8H SHAM/KO

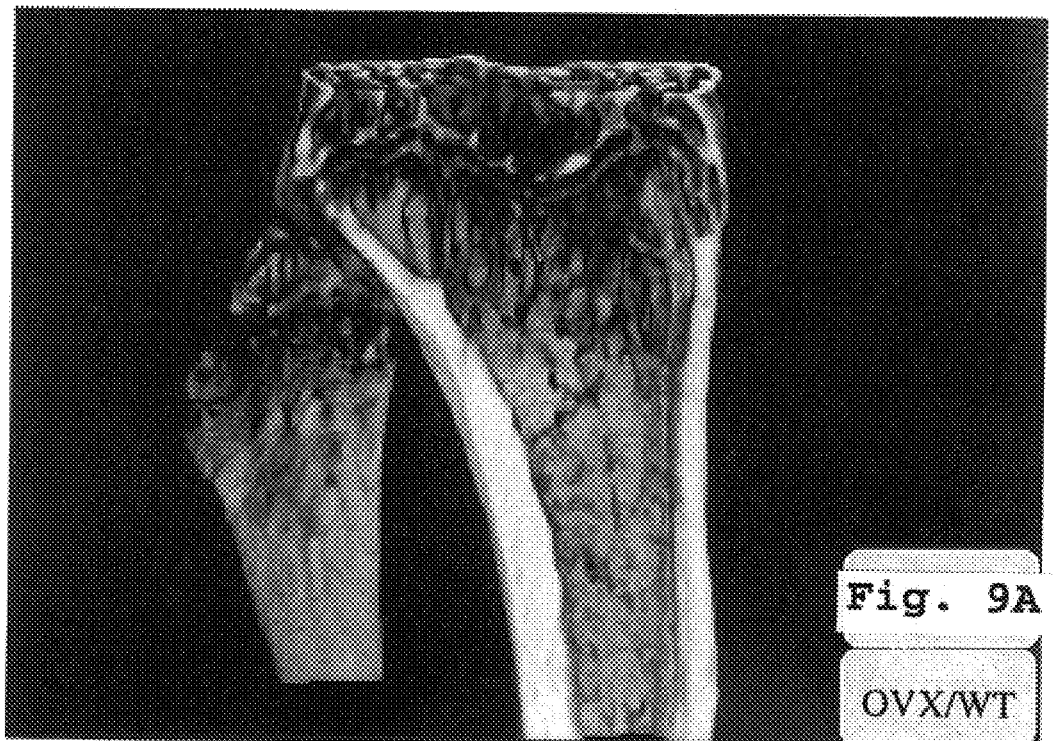
Fig. 9A OVX/WT
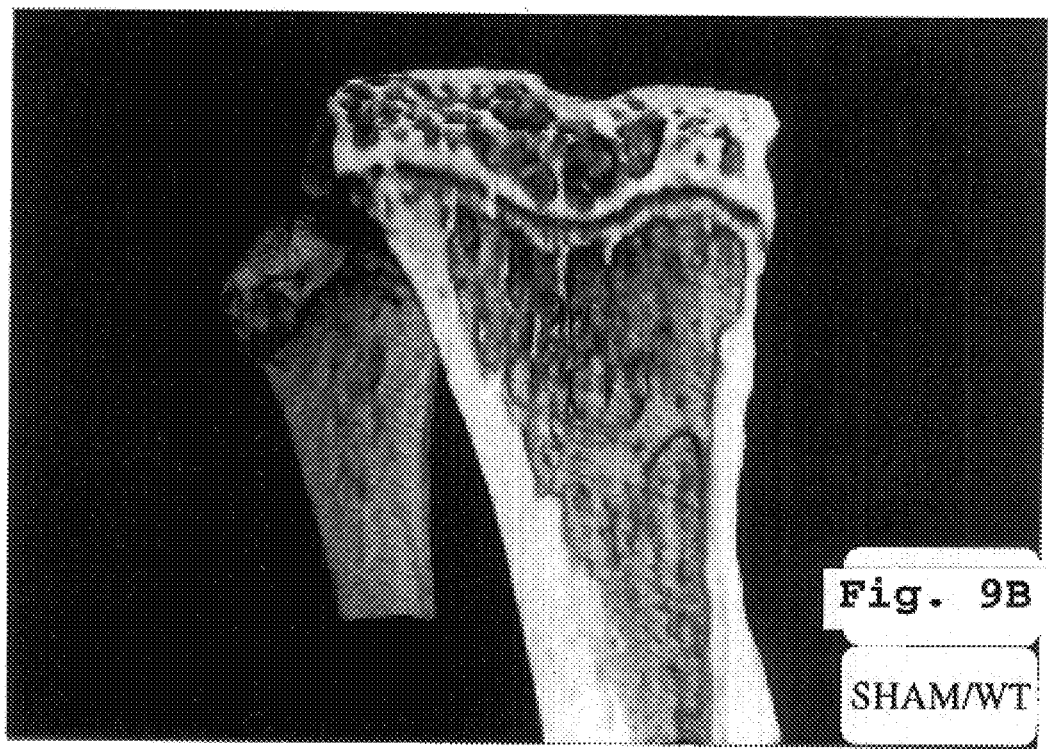
Fig. 9B SHAM/WT

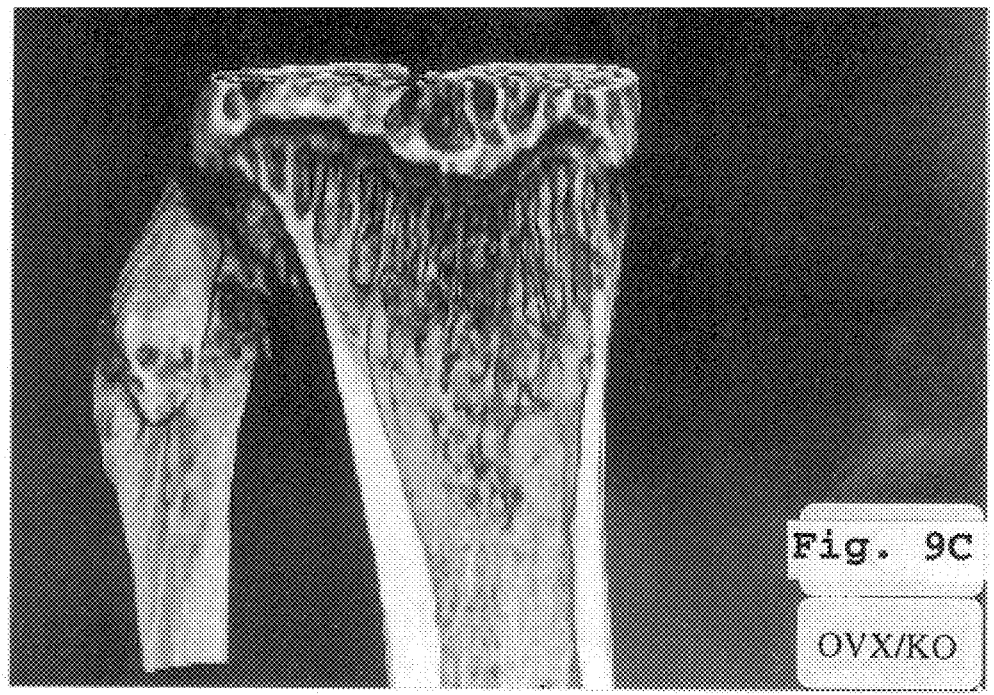
Fig. 9C OVX/KO
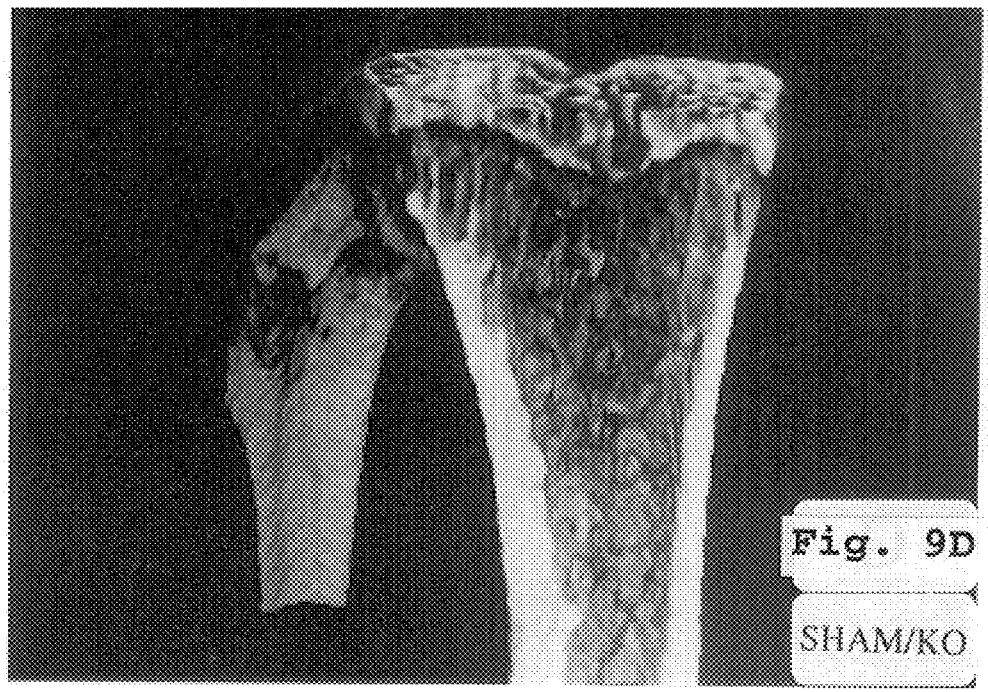
Fig. 9D SHAM/KO

OVX/WT

SHAM/WT

OVX/KO

SHAM/KO

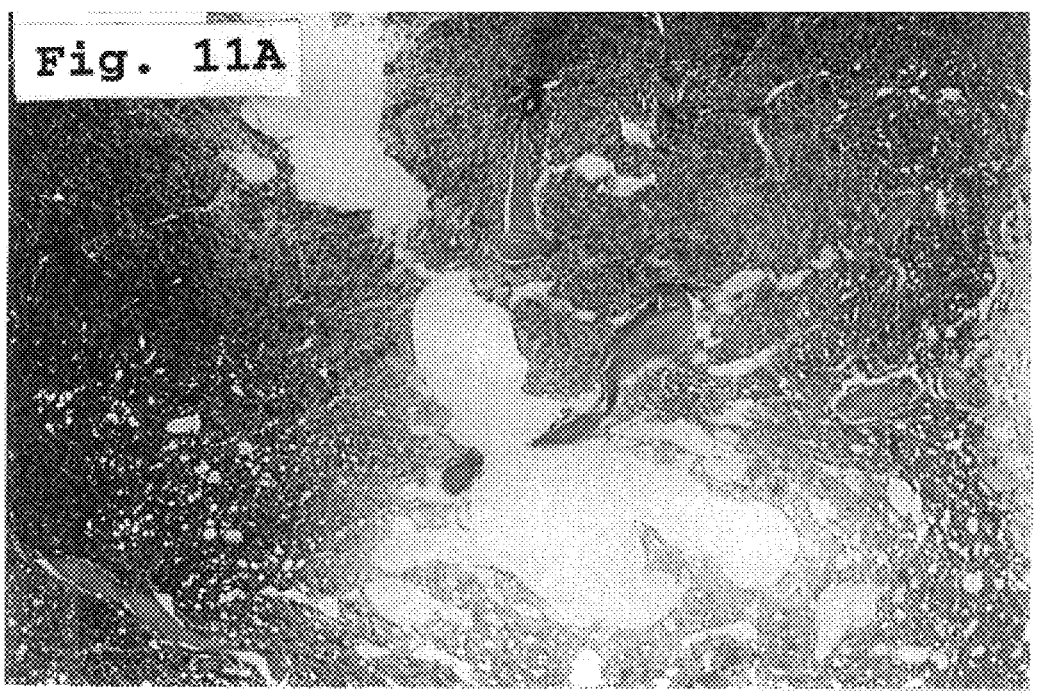
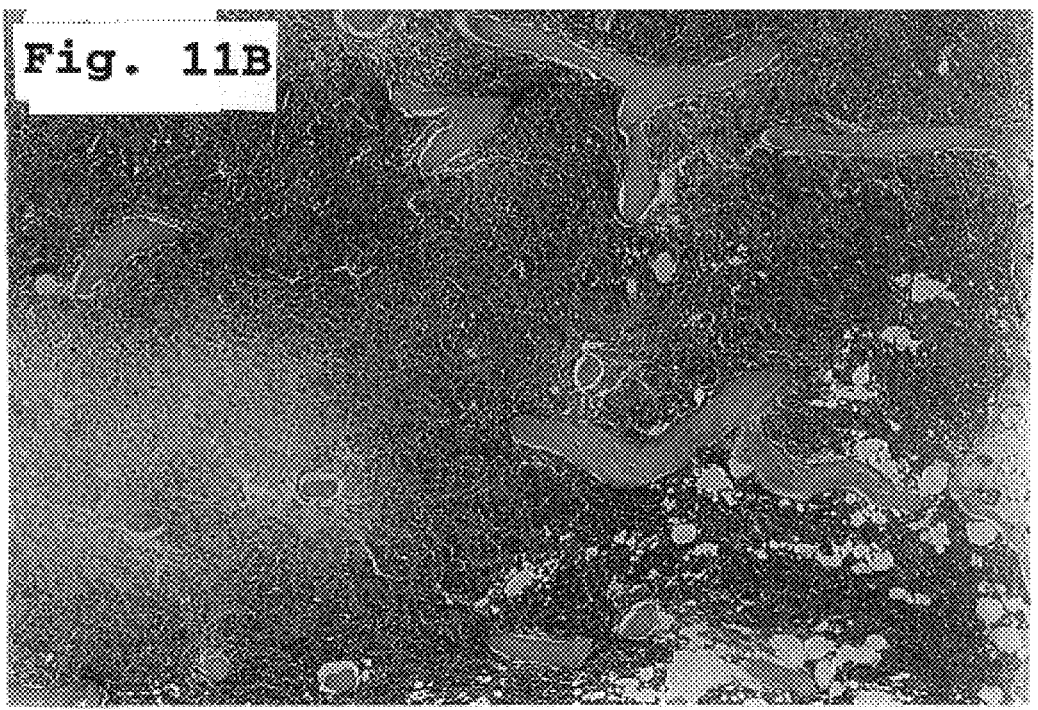

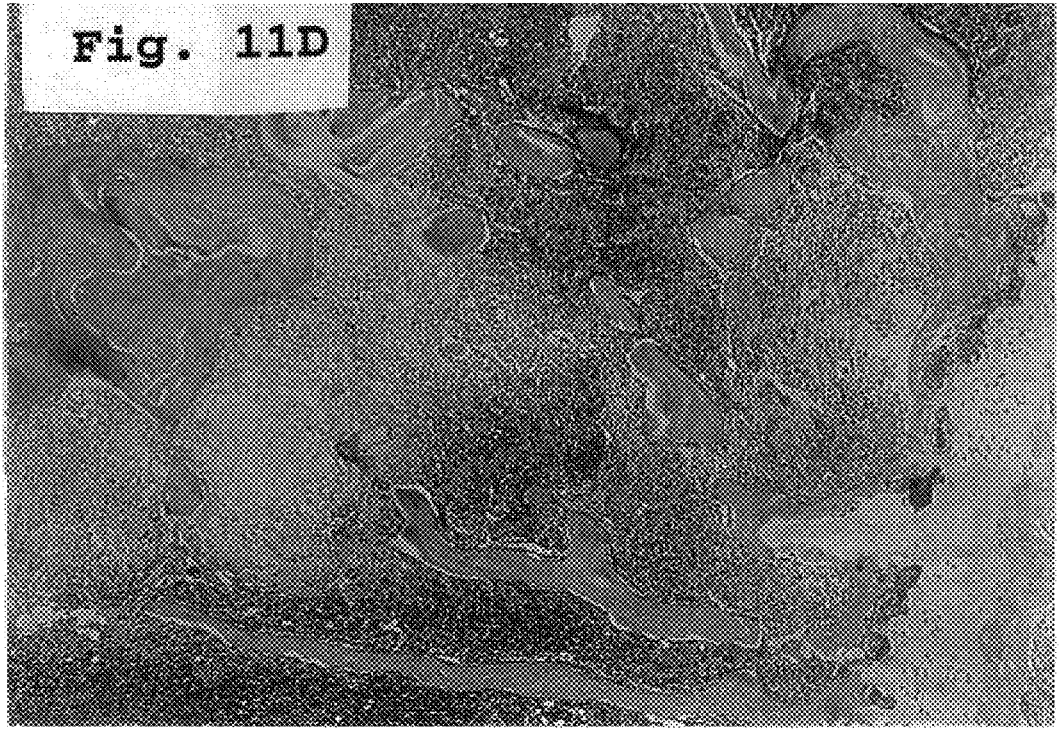

OSTEOPONTIN KNOCK-OUT MOUSE AND METHODS OF USE THEREOF

This application claims priority under 35 U.S.C §119(e) to U.S. Provisional Application No. 60/091,200, filed Jun. 30, 1998.

Pursuant to 35 U.S.C. §202(c) it is acknowledged that the U.S. Government has certain rights in the invention described herein, which was made in part with funds from the National Institutes of Health, Grant Number DC01295.

FIELD OF THE INVENTION

This invention relates the fields of recombinant DNA technology, transgenic animals and signal transduction. More specifically, a transgenic nonhuman animal is provided wherein the osteopontin gene has been altered. Methods of using such animals to assess osteopontin's role in the modulation of cellular activities are also provided.

BACKGROUND OF THE INVENTION

Several publications are referenced in this application by superscript numerals in parentheses in order to more fully describe the state of the art to which this invention pertains. The disclosure of each of these publications is incorporated by reference herein.

Osteopontin (OPN) is a secreted phosphoprotein found in the collagenous extracellular matrix of mineralized tissues and in many body fluids, notably plasma, urine, bile and milk.[1-3] The protein has a GRGDS integrin-binding sequence that interacts with integrins of the $\alpha_v$ class, and it can facilitate attachment of cells to various surfaces, for example during the attachment of osteoclasts to bone.[4,5] Sequence motifs in OPN that have been well conserved among avian and mammalian species include the RGD sequence just N-terminal to a thrombin cleavage site, an Asp-rich sequence with possible importance in binding to calcified tissues, a C-terminal heparin-binding domain, and multiple serine residues in contexts appropriate for phosphorylation by casein kinase II or mammary gland kinase.[6] The synthesis of OPN is induced when T cells are activated,[7] when JB6 epidermal cells are treated with 12-O-tetradecanoyl-phorbol-13-acetate[8] and when Ras becomes activated and cells acquire a metastatic phenotype.[9] Indeed, various experiments have shown that OPN is involved in the metastatic process.[10-12]

In addition to a cell attachment capability, OPN has properties of a cytokine.[7] For example, it can activate c-src and stimulate phosphoinositide 3-kinase activity in target cells.[13,14] OPN can inhibit the induction by lipopolysaccharide and γ-interferon of inducible nitric oxide synthase (iNOS, type II nitric oxide synthase).[15] This inhibition of iNOS transcription correlates with the ability of OPN to protect tumor cells from being killed by activated macrophages,[16,17] suggesting that perhaps this is how OPN contributes to the metastatic phenotype. Osteopontin is produced at high levels by the macrophages found in granulomas of diverse etiology, including those induced by Mycobacterium tuberculosis,[19,20] consistent with its having an anti-inflammatory role. An anti-infectious role has long been suspected because of its association with resistance to certain infectious agents.[7] OPN also induces cellular chemotaxis and haptotaxis,[21,22] and it stimulates the infiltration of monocytes and macrophages to sites of subcutaneous OPN injection,[23] possibly through a mechanism involving CD44.[24] There is a strong association between enhanced OPN expression and monocyte/macrophage infiltration at sites of focal injury in the kidney.[25-27]

Despite the variety of activities attributed to OPN, and its prominence in many normal and pathological tissues, its significance to the vertebrate organism remains to be elucidated. It is frequently found in pathological calcifications such as atherosclerotic plaques,[2] sclerotic glomeruli,[28] and kidney stones.[29,30] Its high expression in osteogenic cells and its accumulation in the calcified extracellular matrices of bone and teeth have been well established, seemingly implicating OPN in the development and remodeling processes of mineralized tissues.[3]

Its presence at mineralized tissue surfaces and interfaces[31] and its facilitation of phagocytosis of OPN-coated particulates are consistent with a role in promoting cell attachment and removal of foreign bodies.[32] Its prominent distribution throughout bone, and in particular its concentration at cement lines, has prompted the suggestion that OPN participates in hard tissue cohesion and may promote interfacial adhesion between apposing substrata.[31,33] Other in vitro studies have identified OPN as a potent inhibitor of hydroxyapatite (calcium phosphate) crystal formation and growth.[33,34].

The precise roles of osteopontin in normal tissue development and maintenance, as well as in embryogenesis and fetal development are not known at this time. Due to the putative biological importance of osteopontin in bone formation and cell attachment, the osteopontin gene is an important target for embryonic stem cell manipulation.

The generation of osteopontin deficient-transgenic mice would aid in defining the normal role(s) of osteopontin and facilitate the use of an animal model of osteopontin deficiency in the design and assessment of chemical approaches to inhibiting or augmenting osteopontin activity. Such osteopontin modified transgenic mice may also be as a source of cells for cell culture.

SUMMARY OF THE INVENTION

This invention provides non-human transgenic animals in which the osteopontin gene has been altered and methods of use thereof. The osteopontin knockout mice of the invention are fertile and develop normally.

Osteopontin plays a role in numerous physiological processes. Osteopontin-related processes include, but are not limited to, bone remodeling, angiogenesis, inhibition of nitric oxide production, renal pathologies, atherosclerosis, monocyte differentiation, osteoporosis and osteoclast function. However, the molecular mechanisms by which osteopontin effectuates these processes have yet to be elucidated.

In a preferred embodiment of the invention, mice transgenic for the osteopontin gene are provided. Such mice may be used to advantage in assays for the identification of therapeutic agents useful for the treatment of osteopontin related pathologies.

In accordance with one aspect of the present invention, it has been discovered that osteopontin knockout mice are resistant to ovariectomized-induced osteoporosis. Thus, these mice may be used to advantage to screen therapeutic agents that inhibit or promote osteoporosis.

In yet another aspect of the invention, it has been discovered that osteopontin-deficient mice are more susceptible to ischemic damage of the kidney than are wild-type mice. Accordingly, methods are provided for assessing therapeutic agents for the treatment such renal disorders.

Osteopontin is a highly conserved plasma protein. While antibodies to the protein exist, antibodies specific for all of the epitopes on the protein are difficult to obtain as these highly conserved regions will not be recognized as "non-self" following antigenic stimulation. The osteopontin knock-out mice of the invention are used in methods for the development of osteopontin-specific monoclonal antibodies. Use of the knock out mice described herein should provide a superior array of antibodies specific for osteopontin.

BRIEF DESCRIPTION OF THE DRAWINGS

The file of this patent contains at least one drawing executed in color. Copies of this patent with color drawings are provided to the Patent and Trademark Office with payment of the necessary fee.

FIG. 3B shows the results of Western blot analysis of OPN protein in various tissues. Protein samples were separated on 12% SDS polyacrylamide gels, and transferred to Immobilon-P membranes. These blots were incubated with goat anti-rat OPN IgG (OP-199, lanes labeled 199) or with control IgG (lanes labeled nIgG), and visualized by enhanced chemiluminescence. Lane 1: 4 µL of medium conditioned by RAW264.7 cells; lanes 2–5: CM—concentrated medium conditioned by primary mouse embryo fibroblast cells, 20 µg protein/lane; lanes 6–9: 10 µl of undiluted mouse urine; and lanes 10–13: 5 µg bone extract protein. OPN from bone migrates more rapidly on this gel than do the other forms of OPN, possibly because of a lower phosphate content. Smearing at the top of the bone +/+ lane (10) incubated with anti-OPN probably represents high molecular weight aggregates of OPN [67]. FIG. 3C shows the presence and relative concentration of cross reacting fragment in −/− bones. Protein extracts from +/+ and −/− bones were fractionated on a 12% SDS-polyacrylamide gel. Left panel: Lane 1: +/+ bone extract, 0.5 µg; lane 2: +/+ bone extract, 0.05 µg; lane 3: +/+ bone extract, 0.01 µg; lane 4: −/− bone extract, 5 µg. This blot was reacted with antiserum 199 as described above. Right panel: Lane 1: +/+ bone extract, 0.5 µg; lane 2: +/+ bone extract, 0.05 µg; lane 3: −/− bone extract, 5 µg; reaction was with antiserum 732. Positions of molecular weight markers (in kD) are shown, and the position of wt OPN is indicated (OPN). The arrows indicate the position of the cross reacting 35-kD species. Antiserum 732 to mouse OPN was made in the $Opn^{-/-}$ mice (Kowalski et al., unpublished data) so that the secondary antibodies used also detect endogenous mouse IgG; the position of these bands in the right panel is indicated by dots.

FIG. 5B shows the results of post-embedding, colloidal-gold immunocytochemistry for OPN in heterozygous (illustrated here) and wildtype mice. The results reveal immunolabeling throughout the bone matrix, particularly in cement lines (CL). FIG. 5C shows the results of immunocytochemistry performed as in FIG. 5B on sections of bone from OPN −/− mice. The absence of colloidal-gold particles over cement lines confirms the lack of OPN in these structures. FIG. 5D shows micrographs of bone matrix immunolabeled for BSP in $Opn^{-/-}$ mice. The data show an otherwise normal distribution of gold particles throughout the bone and also at cement lines (CL). FIG. 5A, Epon section of undecalcified tibia stained with uranyl acetate and lead citrate. FIGS. 5B–5D, LR White sections of decalcified alveolar bone from the mandible immunolabeled for OPN or BSP and counterstained with uranyl and lead.

FIGS. 6A–6E show tartrate-resistant acid phosphatase staining of osteoclasts developing in cultures with ddy osteoblasts[47] as described in methods. FIG. 6A, +/+; FIG. 6B, +/−; FIG. 6C, −/−; FIG. 6D, +/+; FIG. 6E, −/−. FIGS. 6A–C: osteoclasts developed from spleen precursors; FIGS. 6D–E osteoclasts from bone marrow precursors. Original magnification x 40.

FIGS. 9A–9D show three dimensional pictures of the trabecular bone in the tibiae. Three dimensional pictures of the trabecular bones were obtained using the tibiae of the wild type (FIGS. 9A, 9B) or the osteopontin deficient (FIGS. 9C, 9D) mice which are either ovariectomized (FIGS. 9A, 9C) or sham operated (FIGS. 9E, 9D). The micro CT used was Musashi(Nittetsu Elex Co. Ltd.)

FIGS. 11A–11D depict micrographs showing histology of the tibiae of the mice. Wild type (FIGS. 11A, 11B) or osteopontin deficient (FIGS. 11C, 11D) mice were either ovariectomized (FIGS. 11A, 11C) or sham-operated (FIGS. 11B, 11D). Tibiae of the mice were subjected to histological preparation. Paraffin sections were made in the sagittal planes of the tibiae and stained with haematoxylon and eosin.

DETAILED DESCRIPTION OF THE INVENTION

Figure 1:
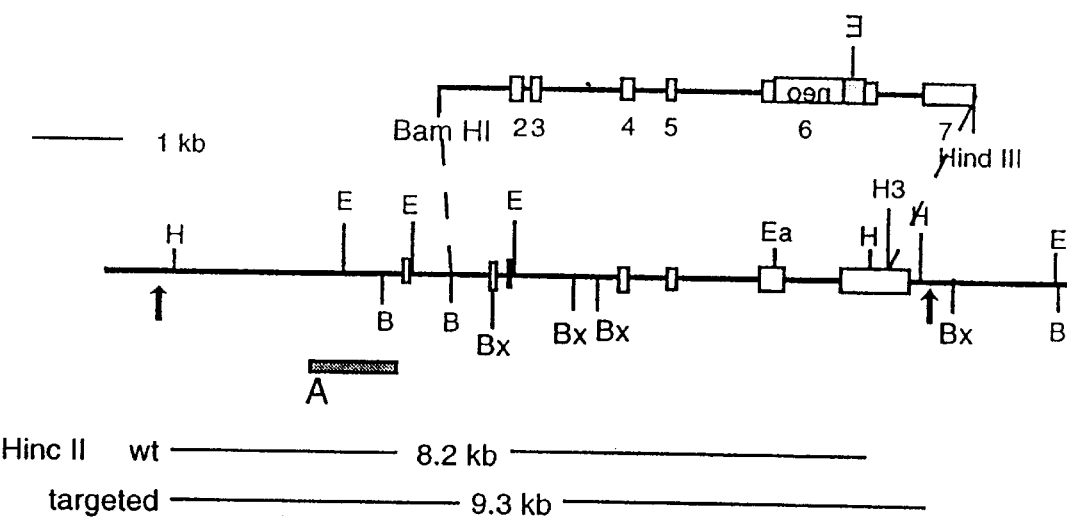
FIG. 1 is a map of the Opn locus and the targeting construct used to create the transgenic mice of the invention. The targeting construct is depicted above the genetic map. Open boxes are exons. The stippled box is the promoter element in the neo cassette, and the open box labeled oen is the neomycin phosphotransferase gene. Dashed lines indicate where the ends of the targeting construct fall in the Opn gene. Selected restriction sites are indicated; H=HincII; E=EcoRI; B=BamHI; Bx=BstXI; Ea=EagI, H3=Hind III, A=sequence used as a probe for osteopontin. The sizes of the expected HincII fragments are indicated.

Osteopontin is an arginine-glycine-aspartate (RGD) containing glycoprotein encoded by the gene secreted phosphoprotein 1 (spp1). ssp1 is expressed during embryogenesis, wound healing, bone remodeling, and tumorigenesis. Osteopontin is involved in a variety of additional physiological processes, including angiogenesis, osteoclast function and osteoporosis. To further understand the role osteopontin plays in these processes, transgenic animals are generated which have an altered osteopontin gene. The alterations to the osteopontin gene are modifications, deletions, and substitutions. Modifications and deletions render the naturally occurring gene nonfunctional, producing a "knock out" animal. Substitutions of the naturally occurring gene for a gene from a second species results in an animal which produces an osteopontin gene from the second species. Substitution of the naturally occurring gene for a gene having a mutation results in an animal with a mutated osteopontin protein. A transgenic mouse carrying the human osteopontin gene is generated by direct replacement of the mouse osteopontin gene with the human gene. These transgenic animals are critical for drug antagonist studies on animal models for human diseases and for eventual treatment of disorders or diseases associated with cellular activities modulated by osteopontin. A transgenic animal carrying a "knock out" of osteopontin is useful for the establishment of a nonhuman model for diseases involving osteopontin regulation.

As a means to define the role that OPN plays in mammalian systems, mice have been generated that cannot make OPN because of a targeted mutational disruption of the Opn gene. These mice develop normally and are fertile. Although no histologically detectable phenotype is apparent in the bones and teeth of mice lacking OPN, the frequency with which spleen and bone marrow cells from Opn−/− mice form osteoclasts in in vitro co-cultures is elevated in comparison with cells from $Opn^{+/+}$ mice.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene.

The altered osteopontin gene generally should not fully encode the same osteopontin protein native to the host animal and its expression product should be altered to a minor or great degree, or absent altogether. However, it is conceivable that a more modestly modified osteopontin gene will fall within the compass of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A type of target cell for transgene introduction is the embryonal stem cell (ES). ES cells may be obtained from pre-implantation embryos cultured in vitro.[68-70] Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated osteopontin genes to selectively inactivate the wild-type gene in totipotent ES cells (such as those described above) and then generate transgenic mice. The use of gene-targeted ES cells in the generation of gene-targeted transgenic mice was described, and is reviewed elsewhere [71-72].

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)5-iodouracil, (FIAU). By this counter selection, the fraction of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Such mice may be used to advantage to identify agents which augment, inhibit or modify the activities of osteopontin. For example, osteopontin knock out mice are resistant to ovariectomized induced osteoporosis. Accordingly, therapeutic agents for the treatment or prevention of osteoporosis may be screened in studies using ovariectomized and non-ovariectomized osteopontin knock out mice. For example, osteopontin knockout mice may be treated with a test compound that induces osteoporosis. Secondary reagents could then be assessed which inhibit or suppress the osteoporotic pathway. Such assays will not only facilitate the identification of agents which regulate osteoporosis, they should also be illustrative of the underlying biochemical mechanisms which underlie the disorder.

Osteopontin knockout mice are also more susceptible to ischemia induced renal damage. Thus in another embodiment of the invention, ischemia of the kidney is induced in osteopontin deficient and wild type mice by clamping the renal artery to prevent blood flow to the kidney. After 30 minutes the clamps are removed and kidney tissue assessed for damage. This damage may be quantified by measuring the levels of blood urea nitrogen and creatinine following reperfusion of the ischemic kidneys. These parameters have been shown to be about two-fold higher in osteopontin deficient animals when compared to wild type controls.

Osteopontin also plays a role in inhibiting formation of nitric oxide. The levels of inducible nitric oxide synthase and nitrotyrosine, an indicator of nitric oxide levels in vivo, were dramatically elevated in post-ischemic, osteopontin deficient kidneys as compared with the post-ischemic wild-type kidneys.

These results implicate osteopontin in protecting the kidney against ischemia-induced damage via a mechanism involving a reduction in nitric oxide production. The data also provide evidence that, in vivo, osteopontin is instrumental in reducing inducible nitric oxide synthase confirming results observed in vitro.

In another embodiment of the invention, osteopontin knockout mice are used to produce an array of monoclonal antibodies specific for osteopontin.

The following methods are provided to facilitate the practice of the present invention.

Generation of Opn−/− Mice

Figure 2:
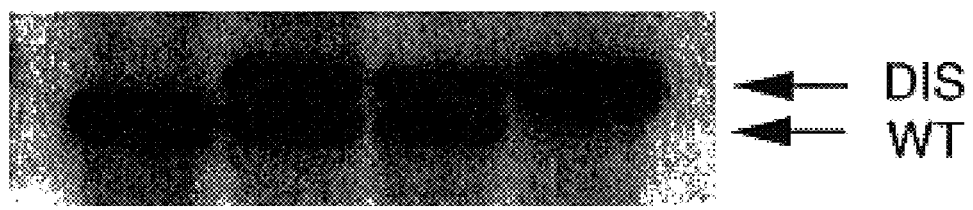
FIG. 2 is a blot showing the results of Southern analysis of DNA from a targeted cell line and from two mice. Genomic DNA was prepared from cells or tail DNA and digested with HincII. The fragments were separated and hybridized to the probe indicated in FIG. 1 (hatched box labeled A) which hybridizes to a region of the Opn gene that is outside the region of homology between the Opn gene and the targeting allele. The positions of the wildtype (WT) and disrupted (DIS) alleles are indicated. Lane 1 is DNA from the parental, wildtype AB2.1 cell line; lane 2 is DNA from the targeted 9B cell line; lane 3 is DNA from a mouse heterozygous for the Opn disruption; and lane 4 is DNA from a mouse homozygous for the Opn disruption.

Osteopontin genomic clones were obtained from a mouse strain 129 genomic library (a generous gift from F. Alt) by screening with a fragment of the Balb/c Opn gene.[37] Positive clones were mapped and a 4.8-kb BamHI- HindIII fragment subcloned into pBluescript. The targeting construct was made by inserting the neo cassette from pMC1 neo[38] into this plasmid at the unique EagI site in exon 6, in the reverse orientation relative to OPN transcription. A thymidine kinase cassette from pMC1TK1[39] was inserted just 3' of the Opn sequences, in the reverse transcriptional orientation. This construct was linearized with BamHI and 100 μg of purified DNA electroporated into $4 \times 10^8$ AB2.1 cells.[40] Transfected cells were plated onto mitomycin-C treated SNL-767 fibroblasts, and drug-resistant cells were selected in G418 plus gancyclovir. Surviving clones were placed into 96-well plates and expanded. Correctly targeted clones were identified by PCR and confirmed by southern blotting as shown in FIG. 2. Cells from two clones that had undergone the desired recombination event were injected into C57Bl/6 blastocysts, which were then implanted into pseudopregnant CD-1 female mice. One of the two clones gave germline transmission of the ES cell phenotype. Genomic DNA from cells or mouse tail fragments was isolated by proteinase K digestion, extracted with phenol, and precipitated with ethanol. Chimeric males were mated to C57Bl/6 females, and the subsequent heterozygous F1 animals were crossed to generate Opn$^{+/+}$ and Opn$^{-/-}$ lines. All animal studies were conducted using protocols approved by the Rutgers Institutional Review Board for the Use and Care of Animals.

Analysis of OPN mRNA and Protein

RNA was prepared by using TriReagent (GibcoBRL, Gaithersburg, Md.). Total cellular RNA was fractionated on 1% agarose gels in the presence of formaldehyde and transferred to Gene Screen Plus (Dupont NEN, Boston, Mass.). These blots were hybridized at 42° C. overnight in the presence of 50% formamide. Western blotting was used to detect OPN in various tissues and body fluids. Serum-free Dulbecco's minimal essential medium, conditioned by mouse embryo fibroblasts for 16 hr, was concentrated about 50-fold prior to analysis. Urine was not concentrated. Protein was extracted from bones as described.[41] Briefly, bones were flash frozen in liquid $N_2$, pulverized, and extracted with 4 M guanidine-HCl in 50 mM Tris-HCl, pH 7.3. This extract was discarded, and the residue was further extracted with 4 M guanidine-HCl in 50 mM Tris-HCl, pH 7.3, containing 0.5 M $Na_2EDTA$, twice for 24 hr each time. The EDTA extracts were combined and the buffer was changed to 6 M urea in 50 mM Tris-HCl, pH 7.3. Proteins were extracted from kidney and lactating mammary glands in RIPA buffer as previously described.[42] Protein concentration was determined by using the bicinchoninic acid assay (Pierce Chemical, Rockford, Ill.). Proteins were separated on 12% SDS-polyacrylamide gels and transferred to Immobilon-P membranes (Millipore, Bedford, Mass.). These blots were blocked with 1% nonfat dry milk and reacted with the indicated antibody preparations. Antibody reactivity was visualized with enhanced chemiluminescence (Amersham, Chicago, Ill.).

Antibodies

Goat anti-rat OPN antiserum 199[21] was kindly provided by Dr. Cecilia Giachelli, and was used in westerns at a dilution of 1:1500, and in immunocytochemistry at a dilution of 1:10. Antiserum 732 is a mouse anti-mouse OPN polyclonal serum developed in our laboratory in the Opn −/− mice (Kowalski et al., unpublished data), and was used in westerns at a dilution of 1:1500 or less. Antiserum to bone sialoprotein (BSP) was LF-6, kindly provided by Dr. Larry Fisher [43].

Bone Histology and Inununocytochemistry

Mandibles, tibiae and calvariae from 2–4 month old mice were fixed in 0.1 M sodium cacodylate-buffered 4% paraformaldehyde/1% glutaraldehyde and analyzed as described.[31] Briefly, bones were left undecalcified or were decalcified for two weeks in 4% disodium EDTA, dehydrated and embedded in Epon or LR White acrylic resin. One-micrometer-thick sections were cut and stained with von Kossa reagent or with toluidine blue for light microscopy; 80–100 nm sections on nickel grids were used for ultrastructural analyses by transmission electron microscopy and for colloidal-gold immunocytochemistry. Post-embedding immunolabeling for OPN[44] was performed using the antibody OP-199[21], and for bone sialoprotein (BSP) using the antibody LF-6 followed by protein A-gold (10–14 nm diameter gold particles) and conventional staining with uranyl acetate and lead citrate. Incubation of sections with preimmune serum, irrelevant polyclonal antibody, or protein A-gold alone served as controls. Morphological observations and immunocytochemical labeling patterns were recorded using a Zeiss Axiophot light microscope and a JEOL TEM 2000 FX II electron microscope operated at 80kV.

Osteoclast Formation in Vitro

Osteoblast cultures were prepared from calvariae of neonatal mice of the indicated strain by sequential collagenase digestion as described[45] and maintained in α-minimal essential medium (MEM) with 10% fetal calf serum (GibcoBRL, Grand Island, N.Y.). Bone marrow cells were obtained by flushing the cells from the medullary cavity of femurs with α-MEM. The dispersed cells were washed, counted, and $2.5 \times 10^5$ cells/cm$^2$ plated on $1 \times 10^4$ osteoblasts in 24-well plates. Similarly, $1 \times 10^5$ spleen cells, obtained as described[46] were plated on osteoblasts in 24-well plates. These cultures were maintained in α-MEM in 10% fetal calf serum in the presence of $10^{-8}$ M 1α,25-dihydroxyvitamin $D_3$ for seven days. Osteoclasts were identified by staining for tartrate-resistant acid phosphatase and classified according to the number of nuclei.[47]

The following Examples are provided to illustrate various embodiments of the invention. They are not intended to limit the invention in any way.

EXAMPLE I

Generation and Characterization of OPN−/− Knock Out Mice

Homologous recombination in embryonic stem cells has been utilized to generate mice with a targeted disruption of the osteopontin (Opn, or Spp1, for secreted phosphoprotein 1) gene. Mice homozygous for this disruption fail to express OPN as assessed at both the mRNA and protein level, although an N-terminal fragment of OPN is detectable at extremely low levels in the bones of −/− animals. The Opn−/− mice are fertile, their litter size is normal and they develop normally. The bones and teeth of animals not expressing OPN are morphologically normal at the level of light and electron microscopy, and the skeletal structure of young animals is normal as assessed by radiography. Ultrastructurally, proteinaceous structures normally rich in OPN, such as cement lines, persist in the bones of the Opn$^{-/-}$ animals. Osteoclastogenesis was assessed in vitro in co-cultures with a feeder layer of calvarial osteoblast cells from wildtype mice. Spleen cells from Opn−/− mice cells formed osteoclasts 3–13 fold more frequently than did control Opn+/+ cells, while the extent of osteoclast development from Opn−/− bone marrow cells was about 2–4 fold more than from the corresponding wildtype cells. Osteoclast development occurred when Opn−/− spleen cells were differentiated in the presence of Opn−/− osteoblasts, indicating that endogenous OPN is not required for this process. These results suggest that OPN is not essential for normal mouse development and osteogenesis, but can modulate osteoclast differentiation.

RESULTS

Derivation of Opn−/− Mice

The targeting construct used to disrupt the Opn gene comprised 4.8 kB of Opn sequence from 129 strain genomic DNA containing a neo cassette inserted into the EagI site in exon 6 (FIG. 1A). This EagI site lies immediately 5' of the RGD sequence, so that any truncated protein made from the 5' end of the gene would lack this integrin-binding sequence. A thymidine kinase-coding sequence in the targeting vector just 3' of the Opn sequence, and in the opposite transcriptional orientation to that of the Opn gene, allowed for enrichment of targeted clones by negative selection.[39] The linearized construct was introduced ist into AB2.1 embryonic stem cells by electroporation, and clones that had undergone the desired homologous recombination event were identified by PCR. The genotype was subsequently confirmed by southern analysis. Correctly targeted clones, grown in the absence of G418, were injected into C57Bl/6 blastocysts. One cell line, 9B, gave rise to male chimeras that were able to transmit the disrupted Opn allele to their offspring. The resulting heterozygous F1 animals were mated to generate animals homozygous for the targeted disruption of the Opn gene, which were obtained in the expected Mendelian ratio. Southern analysis of DNA from the targeted 9B cell line and two mice containing the disrupted Opn allele confirmed that these animals were homozygous for the disrupted Opn allele (FIG. 1B).

Assays for OPN Expression in Mice Homozygous for the Disrupted Opn Gene

To verify that OPN expression was indeed extinguished in the Opn −/− animals, we analyzed Opn mRNA and protein levels in a variety of different tissues and cell preparations (FIG. 2). The probe used in the experiment of FIG. 2A was a fragment of the Opn cDNA extending from the 5' end of the mRNA to the Eag I site in exon 6, the site of insertion of the neo cassette in the targeting construct. This probe will hybridize to any truncated mRNA fragments which might be transcribed from the endogenous promoter in the disrupted Opn gene. No normal-sized or truncated Opn transcripts were detectable in RNA derived from kidneys of the Opn−/− mice. A higher molecular weight RNA species hybridizing with this probe was seen when large amounts of RNA from Opn−/− kidneys were analyzed (FIG. 2B, lane 6). This transcript hybridizes with both 51 and 31 probes, and is seen in RNA preparations from mice of both genotypes. Its identity is at present unknown.

Western blotting of a variety of tissues, fluids, and cells from these mice with the anti-OPN antiserum OP-199 confirmed that OPN protein was not detectable in the Opn$^{-/-}$ animals (FIG. 2B). Samples assayed included medium conditioned by mouse embryo fibroblasts (lanes 2–5), urine (lanes 6–9), and an extract of bone (lanes 10–13). In many cases these results were difficult to interpret because cross reactivity of OP-199 and other antibodies was seen with several unidentified proteins, particularly in the tissue extracts. For this reason, comparisons of identical samples incubated with immune and control IgG are shown FIG. 2B. For example, in lanes 3 and 4, showing conditioned medium from embryo fibroblast cultures, several proteins migrating more rapidly than OPN in the Opn−/− sample exhibited reactivity with the 199 antiserum; however, this reactivity was also seen with the control IgG in lane 4.

In bone extracts from the Opn −/− animals, antisera OP-199 and 732, both specific for OPN, detect a protein migrating with an apparent molecular weight of ~35-kD in long exposures (FIG. 2C). It is likely that this protein represents a truncated form of OPN. In principle, a transcript could be generated from the endogenous OPN promoter and be completely processed to generate a 2.8-kB MRNA containing the neo sequences in exon 6. If this transcript were translated, it would give rise to an amino-terminal fragment of OPN, which would contain sequences represented in exons 2–5 and part of exon 6. Such a protein would not contain the RGD sequence, or the C-terminal half of the protein. We have estimated that the 35-kD protein is present at a level 100–200-fold lower than that of wildtype OPN, and we have been unable to detect it in any body fluids or tissues other than bone. This fragment of osteopontin would be unlikely to have any effect on the phenotype of the animals. First, it is predicted to lack the RGD sequence which has been shown to be important for OPN function in several systems. Second, while this fragment would be expected to retain the poly-Asp sequence, which might allow it to function in mineral binding, its extremely low concentration (FIG. 2C) renders it unlikely that this fragment can have any effect on the bone phenotype. Independent support for this idea comes from observations of animals with a different disruption of the OPN gene in which exons 4 through 7 are deleted[78]. These animals lack the immunoreactive 35-kD OPN fragment, yet their bone morphology is indistinguishable from that described here (FIGS. 3 and 4, and McKee, Rittling and Liaw, unpublished data).

Characteristics of the OPN-deficient Mice

Mice homozygous for the targeted disruption appear phenotypically normal. They are fertile and can lactate, and their litter size is normal. Weights of the animals of the different genotypes between 25 and 52 days of age do not differ significantly (data not shown). Histological examination of liver, spleen, kidney, pancreas, and lung revealed no obvious abnormalities in the Opn$^{-/-}$ animals (data not shown).

Bone Morphology in the Absence of OPN

Figure 3A:
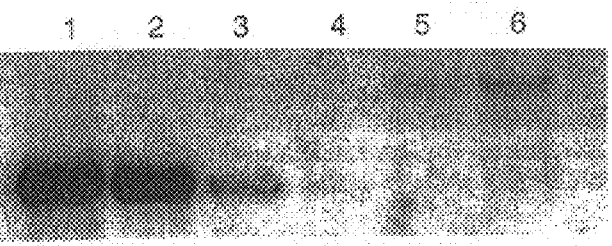
FIGS. 3A, 3B and 3C are Northern and Western blots showing the absence of OPN Expression in $Opn^{-/-}$ Mice. The results of Northern analysis of kidney RNA prepared from mice with different Opn alleles are shown in FIG. 3A. Total RNA was prepared from kidneys of mice of different genotypes and fractionated on an agarose gel. The resulting blot was probed with a fragment of the Opn cDNA extending from the 5' end of the RNA to the EagI site in exon 6. Lane 1: +/+, 5 µg; lane 2: +/−, 5 µg; lane 3: +/−, 0.5 µg; lane 4: +/−, 0.1 µg; lane 5: −/−, 5 µg; lane 6: −/−, 20 µg. Identical results were obtained with a probe representing Opn sequences 3' of the EagI site.
Figure 3B:
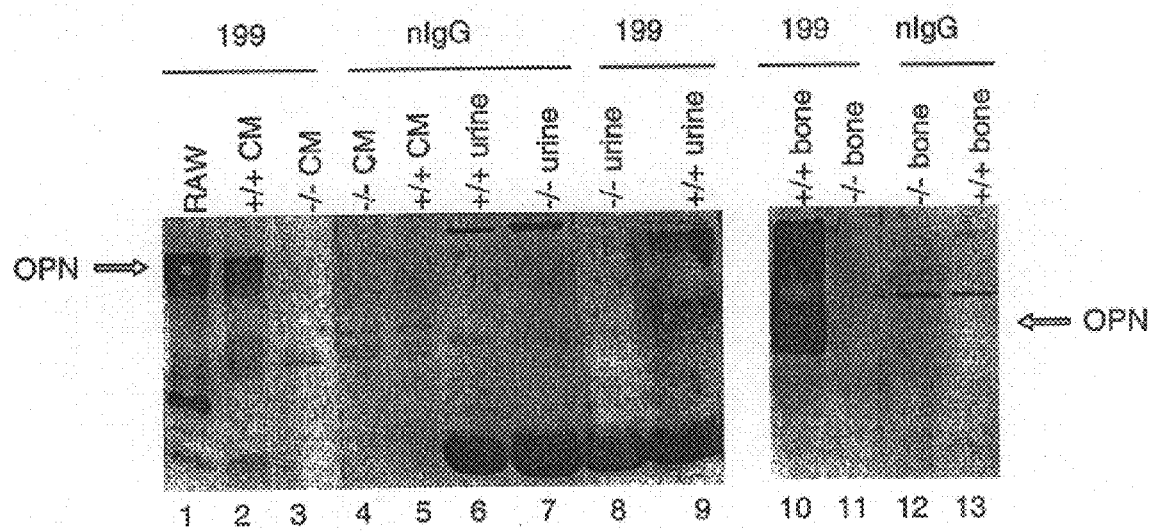
Figure 3C:
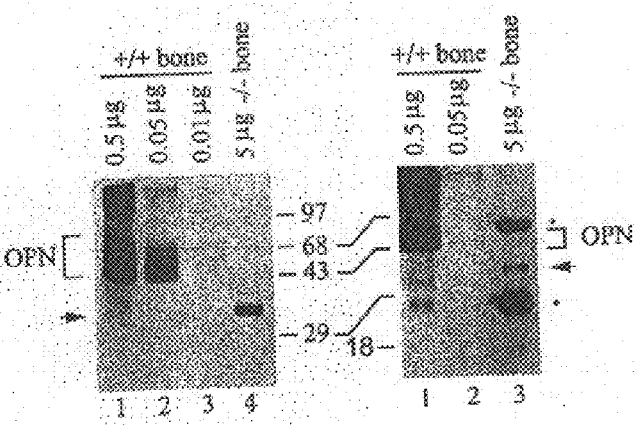

OPN was originally isolated from bone,[48] and its name reflects its presumed importance in this tissue, in which it is especially abundant.[3] We have extensively compared the bones of Opn+/+ and Opn−/− animals using radiography, light and electron microscopy, and ultrastructural immunocytochemistry. The skeletal structure of the Opn−/− animals appeared radiographically normal (data not shown). Morphologically, the cells and extracellular matrix organization and composition of the bones and teeth in the Opn−/− mice were indistinguishable from those of wildtype animals (FIG. 3 and data not shown). In bone, osteogenic cell types were readily identifiable and were present with their expected frequency and distribution. Identical results have been obtained with an independently derived strain of Opn−/− mice (McKee and Liaw, unpublished data). These results lend support to the idea that the cross-reacting 35-kD protein seen on western blots, if it is an OPN fragment, is not responsible for the lack of a phenotype in the bones of the Opn−/− mice. The disruption in the OPN gene in the mutant mice generated by Liaw and coworkers was achieved by a strategy which would not be expected to generate a similar 35-kD fragment[78].

Figure 4A:
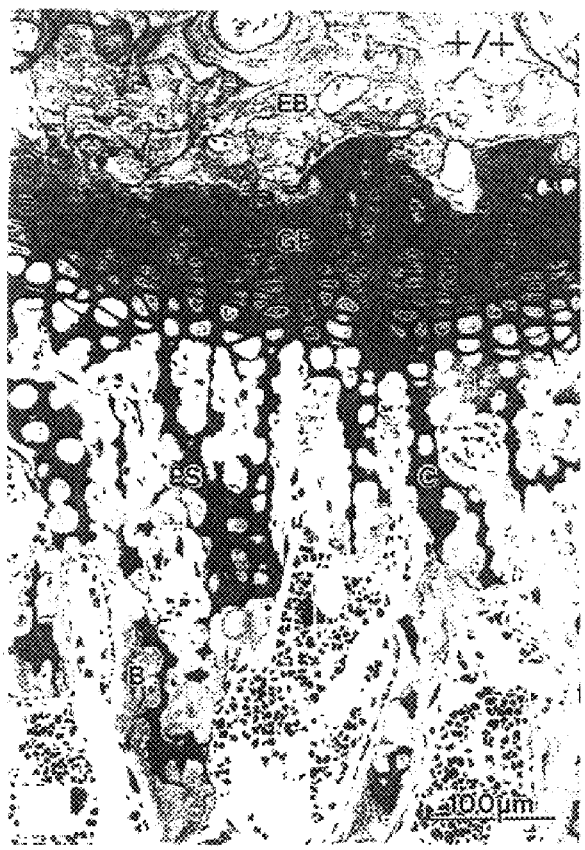
FIGS. 4A and 4B are a pair of micrographs showing the histology of the proximal tibial growth plate in $Opn^{+/+}$ and $Opn^{-/-}$ mice. Light microscopic features of both wildtype (FIG. 4A, $Opn^{+/+}$) and mutant (FIG. 4B, $Opn^{-/-}$) tissues are similar in that the growth plates (GP) subjacent to epiphyseal bone (EB) contain columns of chondrocytes that typically proceed through proliferative and hypertrophic stages. In mice of both genotypes, bone (B) is deposited by osteoblasts onto spicules of calcified cartilage (C) to form the primary spongiosa (PS). These are epoxy resin (Epon) sections obtained from decalcified specimens and stained with toluidine blue.
Figure 4B:
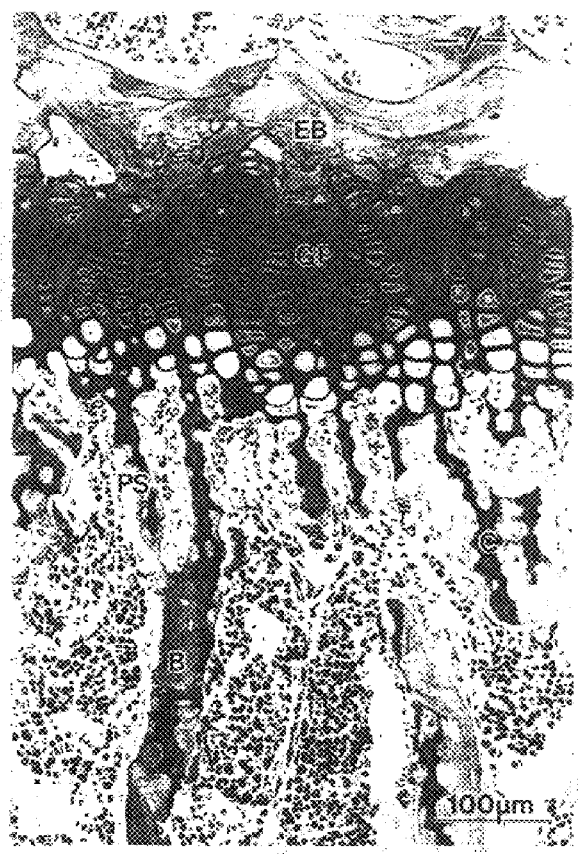

Ultrastructurally, extracellular matrix organization of bone tissue in the mutant mice was unchanged, and prominent organic structures within the bone such as collagen fibrils, cement lines and laminae limitantes were all readily discernable. Calcification of the matrix appeared unaffected by the absence of OPN. Osteoclasts with well-developed ruffled borders and otherwise normal histology were present, and numerous crenated cement (reversal) lines, indicative of bone resorption activity by these cells, were distributed throughout the bone matrix. Colloidal-gold immunocytochemistry for OPN in wildtype mice revealed intense immunolabeling of mineralized matrix in bone, tooth cementum, laminae limitantes at bone surfaces, and cement lines at sites of bone remodeling. However, in the Opn−/− mice, while normal hard tissue architecture and organization were retained (FIG. 4A), cement lines and other structural elements normally known to contain OPN (FIG. 4B) showed a complete absence of immunolabeling for this protein (FIG. 4C). Other noncollagenous extracellular matrix proteins abundant in bone, such as bone sialoprotein (FIG. 4D) and osteocalcin (data not shown), exhibited essentially normal immunolabeling patterns in the OPN-deficient mice.

Figures 5A, 5B, 5C, 5D:
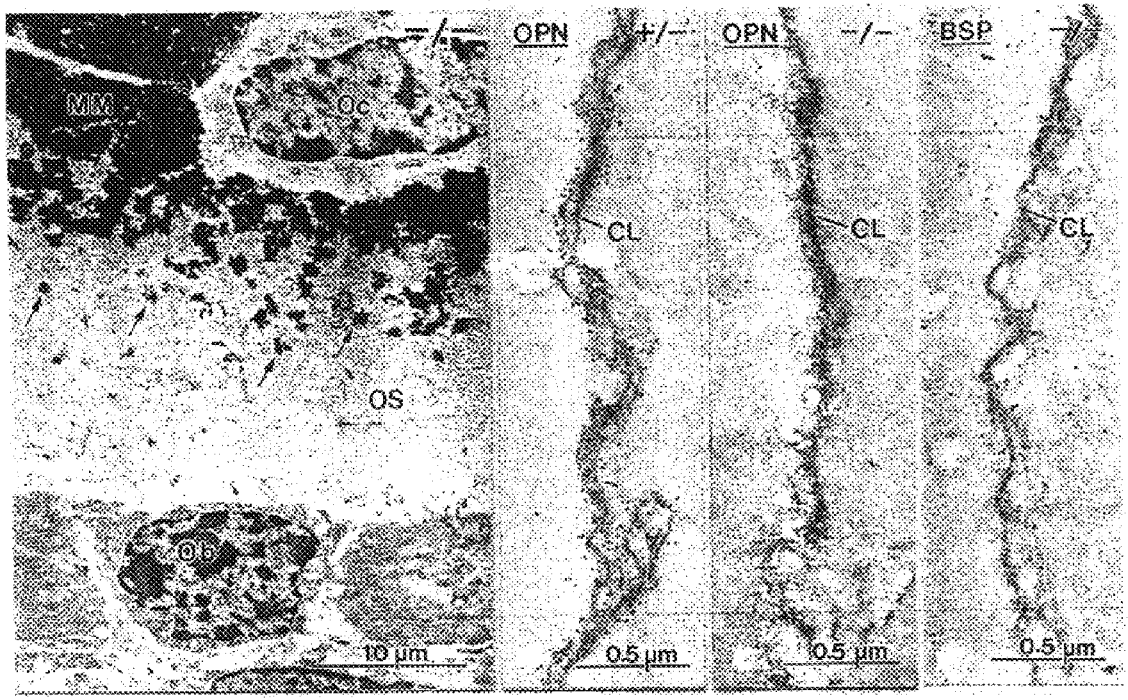
FIGS. 5A–5D are micrographs showing bone ultrastructure and immunocytochemistry in $Opn^{+/-}$ (FIG. 5B) and $Opn^{-/-}$ (FIGS. 5 A,C and D) animals. As observed here by transmission electron microscopy of undecalcified samples of tibia from mutant mice, and as similarly noted for wildtype animals, bone-forming osteoblasts (Ob) secrete a layer of generally unmineralized osteoid matrix (OS) that subsequently calcifies to become the mineralized matrix (MM) proper of bone. As for normal bone, calcification commences as small foci within the osteoid (arrows), with mineral confluence being achieved at the interface between the osteoid and the mineralized matrix—the so called mineralization front. Osteoblast lineage cells become trapped in the matrix and are identified as osteocytes (Oc). See FIG. 5A.
Figure 7:
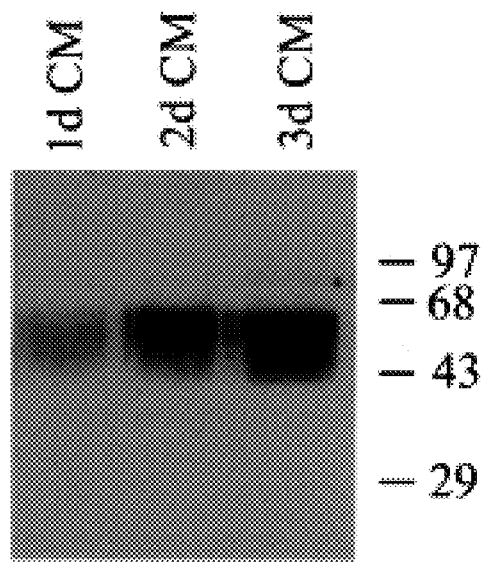
FIG. 7 is an immunoblot showing osteopontin expression in ddy osteoblast cultures. Osteoblasts were prepared from ddy calvaria, and cultured for 8 days. At the end of the culture period the cells were incubated in serum-free medium for an additional 1 day (1d CM), 2 days (2d CM), or 3 days (3d CM) as indicated above the lanes, and this conditioned medium was collected. 15 μl of these conditioned media were fractionated directly on an SDS polyacrylamide gel, transferred to Immobilo-P and reacted with OP-199 IgG as described in the legend to FIG. 3B and Materials and Methods.

Altered Osteoclastogenesis in Vitro OPN has been implicated in osteoclast function[4,3] so the consequences of a lack of this protein on osteoclast differentiation from monocyte precursors was assessed in vitro. When in contact with osteoblasts, and in the presence of 1α,25-dihydroxyvitamin $D_3$, osteoclast precursor cells from bone marrow and spleen can be induced to differentiate into osteoclast-like cells.[45,46] In these coculture systems, cells derived from bone marrow and spleen differentiate in vitro over seven days into multinucleated cells with the characteristics of osteoclasts: they stain for tartrate-resistant acid phosphatase (TRAcP), resorb bone, and bind calcitonin.[49] Spleen cells from Opn$^{-/-}$ animals in such cocultures gave rise to markedly more TRAcP$^+$ cells than did spleen cells from Opn$^{+/+}$ mice (Table 1, FIG. 5). Spleen cells from Opn$^{+/-}$ animals gave an intermediate result. While the absolute number of osteoclasts formed varied among individual animals (as has been previously shown to occur[50]), on average, about 7-fold more multinucleated cells stained for TRAcP after 7 days in culture in the Opn$^{-/-}$ cultures as compared to the Opn$^{+/+}$ cultures (Table 1, and data not shown). Cells derived from the Opn$^{+/-}$ animals were on average 3-fold more efficient at forming osteoclasts than were wildtype cells (Table 1, and data not shown). These TRAcP+ cells derived from Opn−/− spleens were confirmed as osteoclast-like in that they were able to form resorption pits in bone slices (data not shown), and the morphology of these pits was similar for both the Opn+/+and Opn−/− osteoclasts. When bone marrow cells from Opn+/+ and Opn−/− mice were placed in such cocultures with primary osteoblasts derived from wildtype mice (either 129xC57Bl/6 or ddy, Table 1), a similar increase in the numbers of TRAcP+ cells developing in 7 days was observed, although the magnitude of the difference, 2–4 fold increased numbers of TRAcP+ cells in the Opn−/− cultures, was not as great as for the spleen cells.

TABLE I

FORMATION OF TARTRATE-RESISTANT ACID PHOSPHATASE-POSITIVE MULTINUCLEAR CELLS (TRAcP+ MNCs) IN COCULTURE EXPERIMENTS WITH CALVARIAL OSTEOBLASTS

| | | Total TRAcP+ MNC +SD | | |
|---|---|---|---|---|
| tissue source | osteoblast genotype | +/+ | +/− | −/− |
| spleen | +/+a | 66 ± 32 | 349 ± 88 | 857 ± 90** |
| spleen | +/+a | 63 ± 23 | nd | 202 ± 103* |
| bone marrow | +/+b | 521 ± 126 | nd | 2363 ± 225** |
| bone marrow | +/+b | 936 ± 276 | nd | 2276 ± 512** |
| spleen | −/−b | 84 ± 28 | nd | 745 ± 134$ |

TRAcP positive multinuclear cells arising from spleen or bone marrow cells derived from Opn+/+ (+/+ column); Opn+/− (+/− column) or Opn−/− (−/− column) were quantitated after differentiation for seven days in the presence of osteoblasts. All stained cells with 2 or more nuclei in 4 independent wells were counted.
Tissue source refers to the origin of the cell plated in co-cultures with osteoblasts.
a: osteoblasts were derived from mouse strain ddy calvaria,
b: osteoblasts derived from mouse strain 129xc57B1/6 calvaria.
The results are expressed as ± standard deviation.
**$p < 0.001$;
*$p < 0.05$;
$\$p < 0.01$ by Student's t-test.
nd = not determined.

The osteoblast cells used in this coculture system produce OPN at readily detectable levels (FIG. 6), so that the osteoclasts from the Opn−/− spleens were exposed to OPN during the culture period. This observation implies that the observed difference in osteoclast formation is due to differences in the spleen cells themselves, or that OPN plays an autocrine role in this system, such that the osteoclast precursors can distinguish endogenously synthesized from exogenously supplied OPN. To distinguish between these possibilities, spleen cells from Opn−/− mice were differentiated on osteoblasts derived from Opn−/− calvariae (Table 1). The results were similar to those obtained with wildtype osteoblasts, indicating that OPN is not required for this process in excess of the amount provided in the FBS.

Significance of Normal Development in Opn−/− Mice

The osteopontin protein sequence is highly conserved among species,[51] and the protein is expressed by cells in a wide variety of tissues throughout the body.[52] OPN is found in most if not all body fluids, is very abundant in mineralized tissues, and has long been implicated in bone formation and remodeling.[3,53] For these reasons, the apparently normal phenotype of mice lacking osteopontin was unexpected. Opn mRNA is expressed at high levels in kidney, for example, yet the kidneys of the mice which do not express OPN are morphologically normal. We have been unable to detect OPN protein in normal (+/+) kidneys by western blotting (data not shown), which implies that under non pathological conditions, there is little OPN in soft tissues. Thus, while OPN is an ubiquitous component of body is fluids, perhaps acting to prevent mineral precipitation from these solutions,[54,55] it does not appear to play an essential role in the normal processes of soft tissue differentiation or homeostasis. It follows that a lack of OPN in these soft tissues has little consequence to the healthy, unstressed organism. Interestingly, mice with disruptions in genes coding for vitronectin and tenascin, which are also RGD-containing proteins[56,57], or for both OPN and vitronectin [78] similarly develop and grow normally.

Role of OPN in Bone Morphology and Mineralization

OPN is abundant in the mineralized tissues; its ability to bind to calcified matrices is due to its overall acidity, including a poly-Asp stretch, and a high degree of phosphorylation.[58] The accumulation of OPN in cement lines demarcating the reversal site of bone remodeling by osteoclasts, and at bone surfaces—laminae limitantes—where osteocytes, osteoblasts, bone lining cells and osteoclasts routinely interface directly with the extracellular matrix, has led to speculation that OPN regulates cell adhesion and dynamics at bone surfaces.[4,5,32] It has also been proposed that OPN present at cement lines (resting, or reversal, lines) and elsewhere in bone mediates hard tissue integrity by binding various extracellular matrix components as well as mineral, thus linking organic and inorganic phases to provide tissue adhesion/cohesion.[rev: 33]

In the present study, we have documented that morphologically defined structures known to be rich in OPN persist in the bones and teeth of Opn−/− mice, and that a lack of OPN apparently has no effect on either the structure or the distribution of cells within these tissues. While no histologically detectable phenotype is apparent in the mineralized tissues of mice lacking OPN, biochemical and crystallographic studies are in progress to test for differences in bone strength and mineral organization in these animals. Since OPN is a member of a family of RGD-containing proteins, some of which, such as bone sialoprotein, are abundant in bone, it may be that some of these other proteins, or perhaps heretofore unidentified proteins, can subserve the putative function of OPN in its absence.

With regard to extracellular matrix mineralization in bones and teeth, our data suggest either that OPN is not normally involved in the calcification of these tissues or that such hard tissues can utilize alternative calcification strategies not involving OPN. A variety of anionic proteins have been identified as regulators of calcification in vertebrate and invertebrate mineralizing systems.[35,59,60] In light of the vital importance of the vertebrate skeleton in maintaining form and locomotion capability, in defining internal cavities and protecting organs and tissues, and in acting as an ion reservoir for calcium homeostasis, it is reasonable that redundant strategies exist for developing and maintaining hard tissue extracellular matrices such as found in bone.

Function of OPN in Osteoclastogenesis

Although there is no obvious alteration in the morphology or ultrastructure of bone cells and extracellular matrix in the Opn−/− animals, the formation of osteoclast-like cells is enhanced up to 13-fold in cocultures with calvarial osteoblasts when the cells are prepared from the spleen or bone marrow of the Opn−/− animals compared to those from the Opn+/+ animals. This result suggests two possibilities: first, that OPN inhibits the differentiation of osteoclast precursors into osteoclasts in cell culture, or second, that OPN affects the formation or accumulation of osteoclast precursors in the spleen and in the bone marrow. Our observation that osteoclasts are formed with similar efficiencies on wildtype and Opn −/− osteoblasts implies, however, that OPN expression is not required for this differentiation process in vitro, and that the difference observed in vitro reflects differences in the cellular composition of the spleen and bone marrow.

Yamate et al.[61] demonstrated that in cultures of bone marrow cells a specific antiserum to OPN inhibited the formation of TRAcP+ cells, as did RGD-containing peptides, suggesting that the binding of OPN to cell surface integrins is important in the development of osteoclasts in the in vitro system. Our results differ from these observations in that we describe an inhibitory effect of OPN on the process of osteoclast differentiation. The major difference between our experiments and those of Yamate and coworkers is in the culture conditions: our experiments were performed on calvarial osteoblasts while those of Yamate et al. utilized cells from the bone marrow cultures themselves as stromal cells. One possible explanation for these divergent results is that there are multiple differentiation pathways leading to osteoclastogenesis, and the pathway used depends on the specific cellular and molecular composition of the culture system used. We hypothesize, then, that osteopontin plays different roles in the different pathways—stimulating differentiation along one pathway, inhibiting it along another. Indeed, our results demonstrate that OPN is dispensable for the differentiation process in vitro altogether, in that osteoclast formation occurs when Opn −/− spleen cells are cocultured with Opn −/− osteoblasts.

In any case, the alteration in osteoclast precursors that we detect in this assay does not appear to affect osteoclast differentiation in vivo under non-pathological conditions. An expected result of increased osteoclast development in vivo might be an osteoporotic/osteopenic phenotype in the $Opn^{-/-}$ animals, yet this has not been detected. Thus, mechanisms to compensate for a lack of OPN appear to exist in the whole animal, but possibly not in the isolated cell cultures. Additionally, if different pathways of osteoclast differentiation exist in vivo, it may be that the pathway used for osteoclastogenesis during normal bone development does not depend on OPN, while a different pathway is used in pathological situations, in which OPN may have a function.

Function of OPN in Pathological Settings

OPN expression in a variety of tissues is elevated in certain pathologies, and the protein is thought to function in several important aspects of immune cell function. For example, OPN expression is known to be increased in the kidney in association with the interstitial fibrosis occurring with glomerulonephritis, with cyclosporine nephropathy, with angiotensin II-induced tubulointerstitial nephritis, and with hydronephrosis.[2,26,27,62] In each case, OPN was hypothesized to play a role in the recruitment of macrophages to these sites of tissue injury. OPN interacts with macrophages,[23] attenuates their response to specific stimuli,[17] and stimulates IgG and IgM production in mixed cultures of macrophages and B cells.[63] The protein is important in macrophage infiltration in vivo [64], is implicated in macrophage adhesion and may also function in bone wound healing [65] Taken together, these observations implicate osteopontin expression as a cellular response to tissue injury of various sorts.[66] Indeed, Liaw et al. [78] have presented evidence that OPN does have a role in soft tissue remodeling, i.e. wound healing. Since the mice in our colony, housed under specific pathogen-free conditions, are not subject to such pathologies, the effect of an absence of OPN in these animals is minimal.

EXAMPLE II

Osteopontin Knockout Mice are Resistant to Ovarectomy-induced Osteoporosis

As mentioned in the previous example, osteopontin is a ligand for the αvb3 integrin, which is expressed at high levels in osteoclasts and has been implicated in the function and development of these cells. While osteopontin-deficient mice are fertile, develop normally, and exhibit no obvious defects in their mineralized tissues, these mice are resistant to ovariectomy-induced osteopenia. Thus, osteopontin is required for the rapid bone resorption resulting from the estrogen deficiency in ovariectomized mice. Accordingly, the osteopontin-deficient mice of the invention may be used to advantage to screen therapeutic agents that are involved in the development of osteoporosis. In one such assay, therapeutic agents would be administered to ovariectomized and non-ovariectomized osteopontin deficient mice. Agents which promote osteoporosis in the ovariectomized osteopontin deficient mice would then be characterized further. In an alternative assay, therapeutic agents would be administered to non-ovariectomized and ovariectomized wild-type mice. Agents which inhibit osteoporosis in the ovariectomized, wild-type mice, would be characterized further.

Postmenopausal osteoporosis [73] is one of the most common diseases affecting aged women. It is a major health problem with regard to not only the high fracture rates and loss of quality of life of the women but also the economic loss to society. In the United States, the number of patients is estimated to be approximately 12 million and the medical costs are estimated in the billion dollar range. It is well established that withdrawal of estrogen causes loss of bone due to an increase in osteoclastic bone resorption and that supplementation with estrogen can reduce bone loss not only in humans but also in experimental animals. One the critical steps in osteoclastic bone resorption is the attachment of osteoclasts to bone and the subsequent formation of a sealing zone, which can be visualized as a clear zone by electron microscopy[74]. This attachment is a prerequisite for bone resorption since it creates a sequestered microenvironment into which osteoclasts secrete protons, creating an acidic milieu suitable for the dissolution of bone mineral. Osteoclasts also secrete proteases into this sealed environment to digest bone proteins.

Integrins are thought to function in the development of osteoclasts, osteoclastic migration to sites of resorption, and initial attachment to bone as well as formation of the sealing zone in osteoclasts[75]. One of the characteristics of osteoclasts is the high levels of the αvβ3 integrin on the cell surface [76] The functional importance of integrins has been indirectly suggested by the inhibitory effect of disintegrins such as echistatin, which have been shown to block osteoclastic development, osteoclastic attachment and subsequent bone resorption in vitro. Importantly, these disintegrins block bone resorption in vivo[77]. These observations indicate that the αvβ3 integrin plays a critical role in bone resorption. The αvβ3 integrin binds to RGDS-containing proteins such as thrombospondin, fibronectin, vitronectin, fibrinogen, von Willebrand factor and osteopontin. Among those, osteopontin has been considered to be one of the most important candidates for a natural ligand for αvβ3 integrin expressed in osteoclasts based on the in vitro experimental data. Osteopontin is one of the most abundant non- collagenous proteins in bone matrix and is produced by osteoblasts as well as osteoclasts. Osteopontin is also produced by the cells in non-skeletal tissues and has been implicated in tumorigenesis. Substrate-bound osteopontin promotes attachment of osteoclasts while soluble osteopontin can alter calcium levels in osteoclasts and suppress iNOS induction in kidney cells and macrophages. These observations suggest that osteopontin could play a key role in both cell attachment and in controlling subsequent bone cell functions such as resorption. Osteopontin has been observed to be present at high levels in the cement (renewal) lines and the lamina limitans. However, the role of osteopontin in vivo in bone metabolism has not yet been elucidated.

Bone resorption following ovariectomy is a model of post-menopausal osteoporosis. To examine the role of osteopontin in this process, we removed the ovaries of 4.5–6-month-old osteopontin-deficient mice and control mice and examined their bones 4 weeks after the operation. In control experiments, osteopontin-deficient and normal mice were sham-operated. At the four-week time point, the uterine weight of the ovariectomized wild type animals was about 30% of the sham-operated wild type mice. Similarly, the uterine weight of the ovariectomized osteopontin-deficient mice was about 25% of that of the sham operated null mice (Table II). The uterine weights of the sham-operated osteopontin-deficient mice and normal mice were similar. There was no difference in the reduction of uterine weight between osteopontin-deficient mice and wild type mice (Table II) indicating that ovariectomy affects organs such as uterus similarly in both osteopontin-deficient and wild type mice. Likewise, the body weight of the sham-operated or ovariectomized animals was similar in both osteopontin null and wild type mice.

TABLE II

|  | MEAN +/− SD | n |
|---|---|---|
| WT OVX | 0.026* +/− 0.006 | 4 |
| WT SHAM | 0.081 +/− 0.021 | 4 |
| KO OVX | 0.024 +/− 0.008 | 4 |
| KO SHAM | 0.105 +/− 0.039 | 4 |

*uterine weight (gram)

Figure 8C:
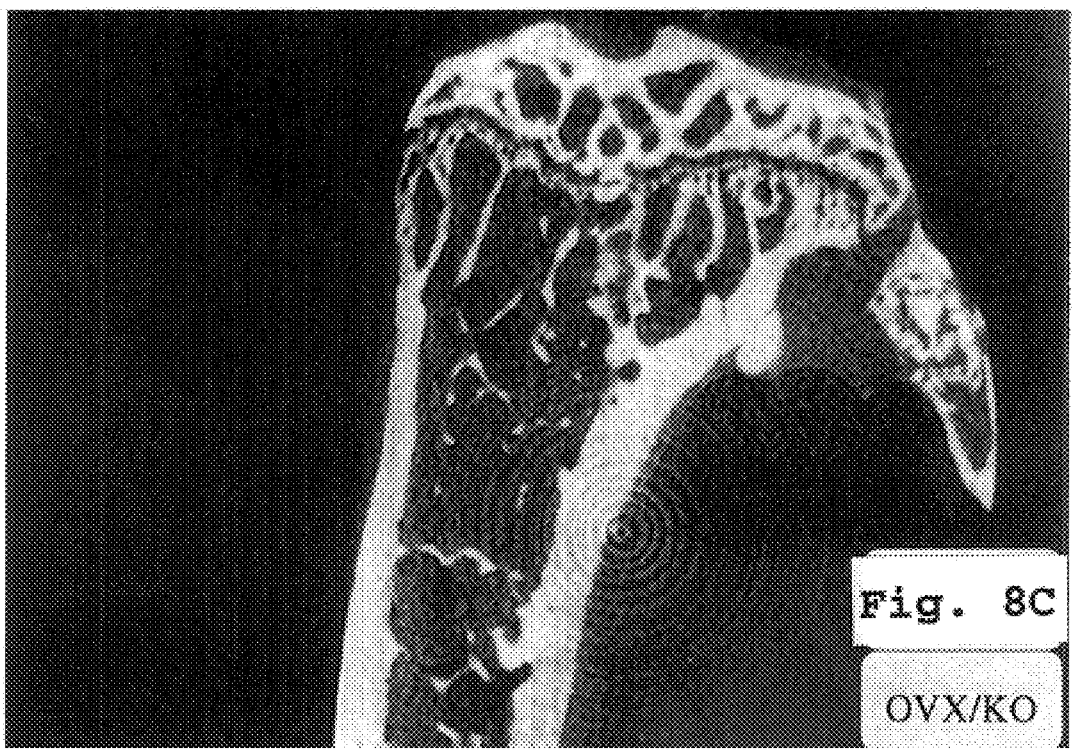
FIGS. 8A–8D show micro-CT analysis of the tibiae of wild-type and osteopontin deficient mice. Wild type (FIGS. 8A, 8B, 8E, 8F) or osteopontin-deficient (FIGS. 8C, 8D, 8G, 8H) mice were either ovariectomized (FIGS. 8A, 8C, 8E, 8G) or sham-operated (FIGS. 8B, 8D, 8F, 8H). Four weeks postoperatively, two-dimensional micro-CT pictures of the tibiae were taken in the mid-sagittal planes as indicated by solid white lines (FIGS. 8E, 8F, 8G, 8H), by using either Musashi (Nittetsu Elex Co. Ltd) or by Scanco microCT-20 system (Scanco Co. Ltd.).
Figure 8D:
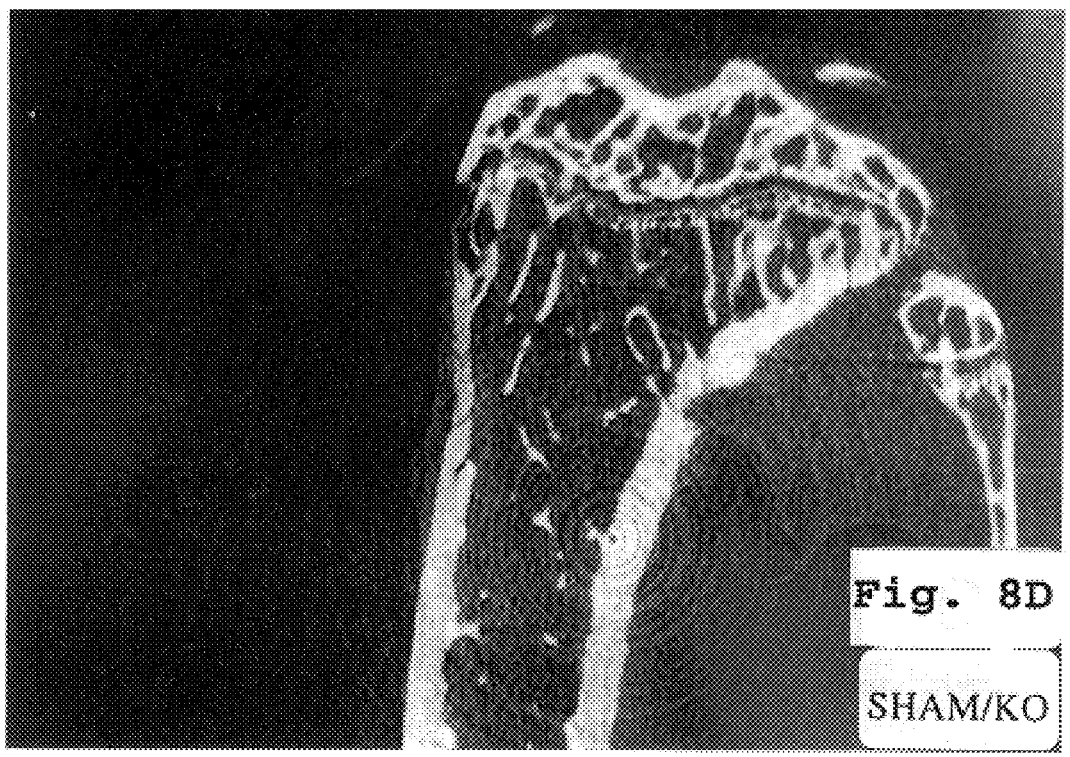
Figure 8E:
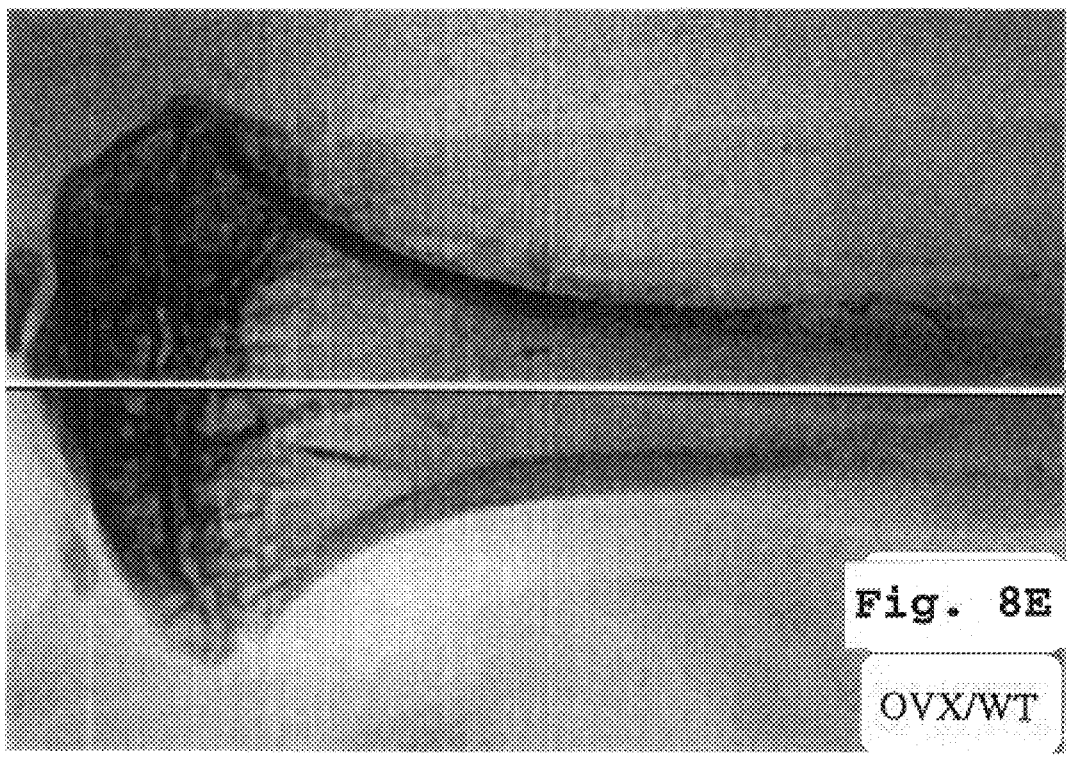
Figure 8F:
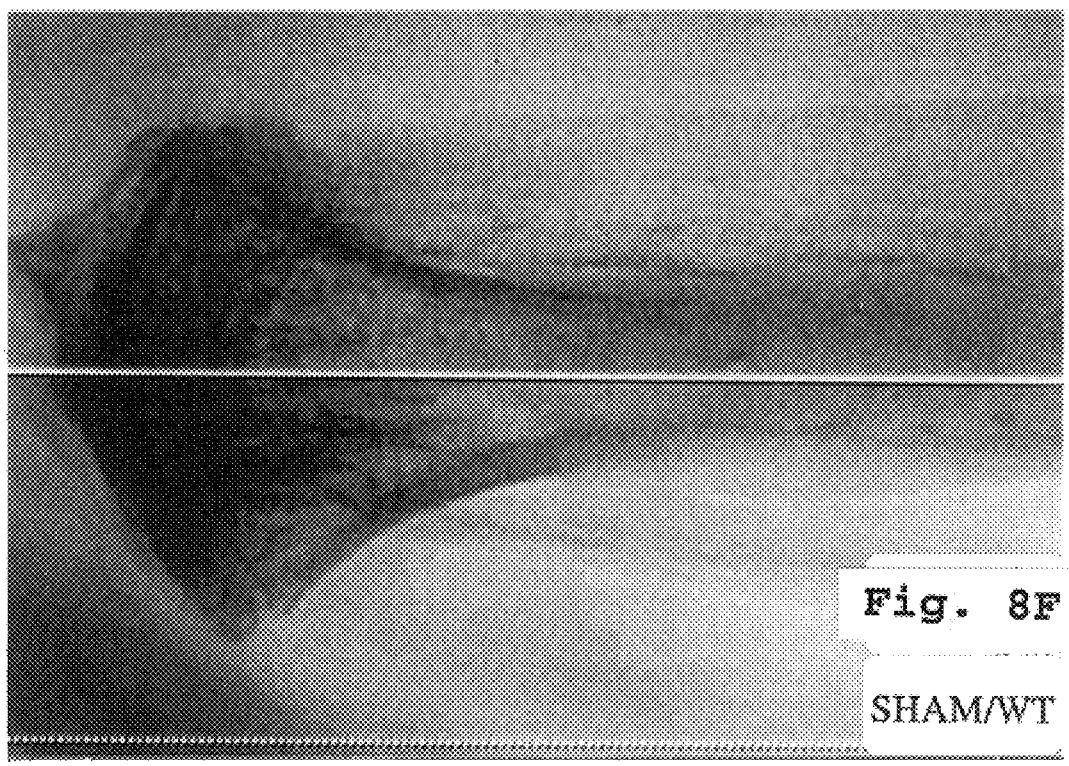
Figure 10A:
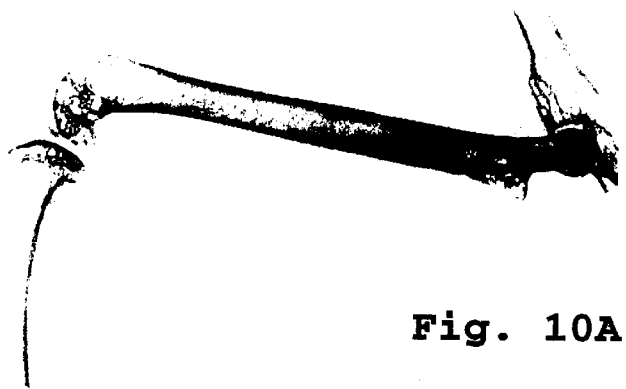
FIGS. 10A–10D show soft x-ray pictures of the tibiae. Wild type (FIGS. 10A, 10B) or osteopontin null (FIG. 10C, FIG. 10D) mice were either ovariectomized (FIGS. 10A, 10C) or sham-operated (FIGS. 10B, 10D). Soft X-ray pictures were taken after dissection of the tibiae. The X-ray was taken by the Softex (Model CMB-2) with exposure time for 2 seconds, and bulb voltage at 50 kV, and bulb current at 25mA using industrial X-ray film FR type (Fuji, Tokyo)
Figure 10B:
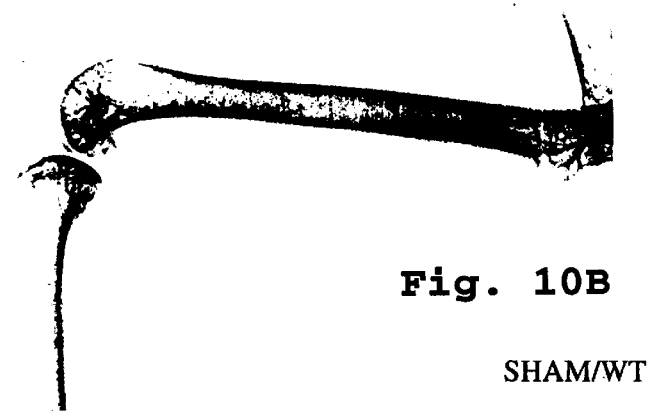
Figure 10C:
Figure 10D:
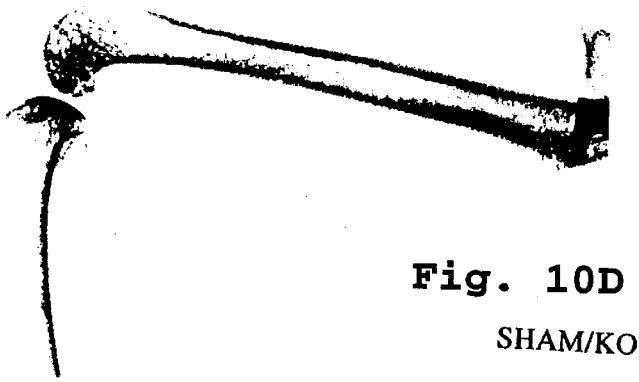

Bone volume was measured quantitatively using micro-computed tomography ($\mu$CT) of the proximal epiphyses of the tibiae. The morphology was evaluated in the mid-sagittal planes as shown in FIGS. 8 A,B,C and D. In two dimensional images, the trabecular bones were seen to be longer and more connected in the sham operated osteopontin-deficient mice (FIG. 8D) compared to the trabecular bones in sham-operated wild type mice (FIG. 8B). The trabecular bones of the ovariectomized wild type mice were sparse (FIG. 8A) compared to, sham operated wild type (FIG. 8B). However, the most striking, feature in the osteopontin-deficient mice was the similar morphology of the trabecular bones between the ovariectomized and sham-operated animals (FIGS. 8C, D). The cutting plane of section is indicated in the FIGS. 8E–H.

Quantitation of the two dimensional (2D-) bone volume in the tibiae shown in FIGS. 8A to 8D using automated image analyzer indicated that the bone volume, expressed as bone area; per tissue area of the wild type mice was reduced by 40% at four weeks following ovariectomy (9.8%) as compared to sham-operated wild type animals (16.1%) while no reduction was observed in the osteopontin-deficient mice between ovariectomy (23.2%) and sham-operation (23.0%) (Table 3). Furthermore, the quantification revealed more bone volume in sham-operated osteopontin-deficient mice (23.0%) than sham-operated wild type mice(16.1%).

TABLE III

|  | MEAN | SD | n |
|---|---|---|---|
| WT OVX | 9.80* | 1.10 | 4 |
| WT SHAM | 16.10 | 1.46 | 4 |

TABLE III-continued

|  | MEAN | SD | n |
|---|---|---|---|
| KO OVX | 23.20 | 4.19 | 5 |
| KO SHAM | 23.00 | 5.60 | 5 |

*bone volume (%)

Three dimensional(3D-) structures of the trabecular bones indicate the reduction in length, number and connectivity of the trabeculae in ovariectomized wild type animals compared to sham-operated wild type while no decrease of these were observed in ovariectomized osteopontin-deficient mice compared to sham-operated osteopontin-deficient mice, supporting the findings observed in two dimensional analyses (FIG. 9). Soft X-ray examination also revealed the preservation of the longer trabecular bones in the epiphyseal and metaphyseal regions of the osteopontin-deficient mice compared to the wild type and ovariectomy reduced the trabecular bones in wild type mice but not in osteopontin-deficient mice (FIG. 10). The reduction is observed mainly in epiphyseal and metaphyseal bone area, although it is also observed in the ends of the mid shaft area in ovariectomized wild type. On the other hand, osteopontin-deficient mice show small trabeculation which extends into the diaphyseal region. This extended trabeculation starting from the metaphysis and continuing into the ends of the diaphyses was not reduced even after ovariectomy in osteopontin-deficient mice (FIG. 10). Histological sections also revealed that more bone volume in ovariectomized osteopontin-deficient mice compared to the ovariectomized control (FIG. 11). Bone islands are apparently more and longer in osteopontin-deficient mice in both sham and ovariectomized animals. Cellularity in the bone marrow was similar between the wild type and osteopontin-deficient mice regardless of the ovariectomy or sham operation.

As reported previously, bone marrow and spleen cells prepared from these osteopontin-deficient mice differentiated into osteoclasts in vitro in the presence of osteoblasts and vitamin D. We also showed that the number of osteoclasts generated in vitro in cocultures of cells prepared from osteopontin-deficient bone marrow and spleen with the osteoblasts from the calvariae of osteopontin-deficient mice was significantly greater than the number of osteoclasts developed in the cocultures of the cells prepared from the wild type mice. See Example I. These results indicate that there is no defect in osteoclastogenesis in the osteopontin-deficient estrogen-sufficient mice. Furthermore, these in vitro generated osteoclasts could resorb bone slices prepared from normal bovine femora. It seems that osteopontin-deficient mice are resistant to the ovariectomy-induced bone resorption not because of the lack of osteopontin produced by the osteoclasts which are resorbing bones but rather because of altered osteoclast regulation in the absence of osteopontin.

The 2D-pattern, radiographical density and 3D-$\mu$CT morphology of the remaining trabecular bones of the ovariectomized osteopontin-deficient mice were similar to those of the sham operated osteopontin-deficient mice. The data suggest that the main defect induced by osteopontin-deficiency is a reduction in the ovariectomy-induced osteoclastic bone resorption activity. Our observations on the resistance against ovariectomy-induced bone resorption in osteopontin-deficient mice by itself clearly indicate the importance of osteopontin in this estrogen-deficiency-induced osteoporosis model. The next step, currently in progress is to understand how the loss of osteopontin leads to such resistance to bone resorption in vivo.

In summary, we have demonstrated that osteopontin-deficient mice are resistant to bone resorption induced by ovariectomy. A similar resistance to ovariectomy induced osteopenia was also observed in opn−/− mice generated in a pure 129 Sv background (data not shown). Whether this is true for human post-menopausal osteoporosis will require further investigation in humans. As of now, there is no information regarding osteopontin deficiency in humans, who might be expected to show resistance to post-menopausal osteoporosis. Genetic analysis of osteopontin gene polymorphism may predict certain patients who could have high or low risk of post menopausal bone loss. If osteopontin does play a role in human post menopausal osteoporosis, it could provide further support for the endeavor to develop anti-bone-resorptive drugs, particularly measures to suppress the action of OPN.

EXAMPLE III

Use of Osteopontin Knockout Mice for the Generation of Osteopontin Specific Monoclonal Antibodies As mentioned in the previous examples, osteopontin is a widely expressed protein that has been conserved throughout evolution. The extensive similarity of osteopontin proteins among species presents certain problems for the generation of osteopontin-specific monoclonal antibodies. Antibodies are generated in response to exposure to foreign antigens. The foreign antigens must be recognized as "non-self" before an immune response will be mounted. The osteopontin knock out mice of the invention can be used to advantage for the production of osteopontin antibodies as these animals do not express native osteopontin. Antibodies so generated will provide a useful research tool for intracellular localizations, epitope mapping and immunoprecipitation studies for characterizing those proteins that form intracellular associations with osteopontin. This concept may also be expanded to encompass antibodies specific for any highly conserved plasma protein. Knock out mice having a null mutation for the gene encoding the plasma protein of interest may be utilized for the generation of a wide array of monoclonal antibodies immunospecific for those proteins. Utilization of knock out mice for this purpose ensures that the immunizing protein antigen will be recognized as non-self and therefore invoke a powerful immune response.

Additional potential applications for the antibodies of the invention include assays to determine whether a particular epitope on the osteopontin protein has been modified. Such antibodies may be used to advantage to assess post-translational modifications or modifications associated with a particular disease state, such as particular cancers, certain kidney or vascular pathologies or immune system disfunctions. The antibodies of the invention may also be utilized to inhibit osteopontin action. For example, loss of bone during osteoporosis appears to require the presence of osteopontin in the bone. A monoclonal antibody immunologically specific for a determinant critical for this interaction may prevent osteopontin from stimulating the bone resorption that occurs during osteoporosis. As mentioned previously, osteopontin inhibits nitric oxide production. In certain inflammatory conditions where nitric oxide production is required or beneficial, a monoclonal antibody specific for osteopontin might prevent osteopontin from inhibiting this beneficial nitric oxide production. Finally, the monoclonal antibodies of the invention may be used to quantify various species of osteopontin, for example in ELISA reactions. It is likely that osteopontin levels in plasma deviate from normal with particular disease states. Thus, the ability to easily and accurately quantify osteopontin levels would be clinically useful.

Polyclonal antibodies can be raised by administration of osteopontin to the knockout mice of the invention, using known immunization procedures. Usually a buffered solution of the antigen accompanied by Freund's adjuvant is injected subcutaneously at multiple sites. A number of such administrations at intervals of days or weeks is usually necessary. A number of animals, for example from 3 to 20, is so treated with the expectation that only a small proportion will produce good antibodies. The antibodies are recovered from the animals after some weeks or months.

The use of monoclonal antibodies is particularly preferred because they can be produced in large quantities and the product is homogeneous. The preparation of hybridoma cell lines for monoclonal antibody production derived by fusing an "immortal" cell line and lymphocytes sensitized against the immunogenic preparation can be done by techniques which are well known to those who are skilled in the art. See, for example, Doullard, J. Y. and Hoffman, T., "Basic Facts About Hybridomas" in Compendium of Immunology, vol. II, L. Schwartz (ed.) (1981); Kohler, G. and Milstein, C., Nature, 256:495–497 (1975); Koprowski, et al., European Journal of Immunology, 6:511–519; Koprowski et al., U.S. Pat. No. 4,172,124; Koprowski et al., U.S. Pat. No. 4,196,265; and Wands, U.S. Pat. No. 4,271,145; the teachings of which are herein incorporated by reference.

Unlike preparation of polyclonal sera, the choice of animal for monoclonal antibody production is dependent on the availability of appropriate "immortal" lines capable of fusing with lymphocytes thereof. Mouse and rat have been the animal of choice in hybridoma technology and preferably used. Humans can also be utilized as sources of sensitized lymphocytes if appropriate "immortalized" cell lines are available. For the purpose of the present invention, the osteopontin knockout mice may be injected with approximately 0.1 mg to about 20 mg of purified osteopontin or fragments thereof. Usually the injecting material is emulsified in Freund's complete adjuvant. Boosting injections may also be required. The detection of antibody production can be carried out by testing the antisera with appropriately labeled antigen, as required by radioimmunoprecipitation, or with capture complex, as required by a variety of solid phase immunoassays including competitive ELISA. Lymphocytes can be obtained by removing the spleen or lymph nodes of sensitized animals in a sterile fashion and carrying out cell fusion. Alternatively, lymphocytes can be stimulated or immunized in vitro, as described, for example, in C. Reading, J. Immunol. Meth., 53:261–291, (1982).

A number of cell lines suitable for fusion have been developed, and the choice of any particular line for hybridization protocols is directed by any one of a number of criteria such as speed, uniformity of growth characteristics, absence of immunoglobulin production and secretion by the nonfused cell line, deficiency of metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobulin. Included among these are the following mouse myeloma lines: MPC sub 11-X45-6TG, P3-NS1-1-Ag4-1. P3-X63-Ag8, or mutants thereof such as X63-Ag8.653, SP2-O-Ag14 (all BALB/c derived), Y3-Ag1.2.3 (rat) and U266 (human).

Cell fusion can be induced either by virus, such as Epstein-Barr or Sendai virus, or by polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1000 to 6000 da. The ratio between lymphocytes and malignant cells is optimized to reduce cell fusion among spleen cells and a range of from about 1:1 to about 1:10 (malignant cells:lymphocytes) gives good results.

The successfully fused cells can be separated from the myeloma line by any technique known in the art. The most common and preferred method is to choose a malignant line which is Hypoxanthine-Guanine Phosphoribosyltransferase (HGPRT) deficient, which will not grow in an aminopterin-containing medium used to allow only growth of hybrids and which is generally composed of hypoxanthine $1\times10^{-4}$ M, aminopterin $4\times10^{-7}$ M and thymidine $1.6\times10^{-5}$ M, commonly known as HAT medium. The fusion mixture can be grown in the HAT-containing culture medium immediately after the fusion. Cell culture usually entails maintenance in HAT medium for one week and then feeding with either regular culture medium or hypoxanthine, thymidine-containing medium.

The growing colonies are then tested for the presence of antibodies that recognize osteopontin. Detection of hybridoma antibodies can be performed using an assay where the capture complex is bound to a solid support and allowed to react with hybridoma supernatants containing putative antibodies. The presence of antibodies may be detected by direct ELISA techniques using a variety of indicators. Most of the common methods are sufficiently sensitive for use in the range of antibody concentrations secreted during hybrid growth.

The present inventors have successfully generated a panel of monoclonal antibodies immunologically specific for osteopontin using the knock-out mice of the invention. Two approaches have been utilized. Antibodies have been raised against murine GST-tagged osteopontin. Clones secreting these antibodies have been designated AKMZA1, AKM4AG9, AKM2C5. Antibodies have also been raised against human His-tagged osteopontin. Clones secreting these antibodies have been designated AKM1G4, AKM8B3, and AKM10F6.

REFERENCES

1. Denhardt D T, Guo X 1993 Osteopontin: a protein with diverse functions. FASEB J 7:1475–1482.
2. Giachelli C M, Schwartz S M, Liaw L 1995 Molecular and cellular biology of osteopontin: potential role in cardiovascular disease. Trends Cardiovasc Med 5:88–95.
3. Butler W T, Ridall A L, McKee M D 1996 Osteopontin. In: Bilezekian, J P, Raisz, L G, Rodan, G A (eds) Principles of Bone Biology, Academic Press, San Diego, pp.167–181.
4. Reinholt F P, Hultenby K, Oldberg C, Heinegård D 1990 Osteopontin—a possible anchor of osteoclasts to bone. Proc Natl Acad Sci USA 8:4473–4475.
5. McKee M D, Nanci A 1995 Osteopontin and the bone remodeling sequence. Colloidal-gold immunocytochemistry of an interfacial extracellular matrix protein. Ann NY Acad Sci 760:177–189.
6. Sørensen E S, Højrup P, Petersen T E 1995 Post-translational modification of bovine osteopontin: identification of twenty-eight phosphorylation and three O-glycosylation sites. Protein Sci 4:2040–2049.
7. Patarca R. Saavedra R A, Cantor H 1993 Molecular and cellular basis of genetic resistance to bacterial infection: the role of the early T-lymphocyte activation-1/osteopontin gene. Crit Rev Immunol 13:225–246.
8. Smith J H, Denhardt D T 1987 Molecular cloning of a tumor promoter-inducible mRNA found in JB6 mouse epidermal cells: Induction is stable at high, but not at low, cell densities. J Cell Biochem 34:13–22.
9. Craig A M, Bowden G T, Chambers A F, Spearman M A, Greenberg A H, Wright J A, McLeod M, Denhardt D T 1990 Secreted phosphoprotein mRNA is induced during multi-stage carcinogenesis in mouse skin and correlates with the metastatic potential of murine fibroblasts. Int J Cancer 46:133–137.
10. Gardner, HAR, Berse B, Senger D F 1994 Specific reduction in osteopontin synthesis by antisense RNA inhibits the tumorigenicity of transformed Rat1 fibroblasts. Oncogene 9:2321–2326.
11. Feng B, Rollo E E, Denhardt D T 1995 Osteopontin (OPN) may facilitate metastasis by protecting cells from macrophage NO-mediated cytotoxicity: evidence from cell lines down-regulated for OPN expression by a targeted ribozyme. Clin Exp Metastasis 13:453–462.
12. Oates A J, Barraclough R. Rudland P S 1996 The identification of osteopontin as a metastasis-related gene product in a rodent mammary tumour model. Oncogene 13:97–104.
13. Chellaiah M, Fitzgerald C, Filardo E J, Cheresh D A, Hruska KA 1996 Osteopontin activation of c-src in human melanoma cells requires the cytoplasmic domain of the integrin $\alpha_v$-subunit. Endocrinology 137:2432–2440.
14. Chellaiah, M, Hruska K 1996 Osteopontin stimulates gelsolin-associated phosphoinositide levels and phosphatidylinositol triphosphate-hydroxyl kinase. Mol Biol Cell 7:743–753.
15. Hwang, S-m, Lopez C A, Heck D E, Gardner C R, Laskin D L, Laskin J D, Denhardt D T 1994 Osteopontin inhibits induction of nitric oxide synthase activity by inflammatory mediators in mouse kidney epithelial cells. J Biol Chem 269:711–715.
16. Rollo E E, Denhardt D T 1996 Differential effects of osteopontin on the cytotoxic activity of macrophages from young and old mice. Immunology 88:642–647.
17. Rollo E E, Laskin D L, Denhardt D T 1996 Osteopontin inhibits nitric oxide production and cytotoxicity by activated RAW264.7 macrophages. J Leukoc Biol 60:397–404.
18. Denhardt D T, Chambers A F 1994 Overcoming obstacles to metastasis—Defenses against host defenses: Osteopontin (OPN) as a shield against attack by cytotoxic host cells. J Cell Biochem 56:48–51.
19. Carlson I, Tognazzi K, Manseau E J, Dvorak H F, Brown L F 1997 Osteopontin is strongly expressed by histiocytes in granulomas of diverse etiology. Lab Invest 77:103–108.
20. Nau G J, Guilfoile P, Chupp G F, Berman J S, Kim S J, Kornfeld H, Young R A 1997 A chemoattractant cytokine associated with granulomas in tuberculosis and silicosis. Proc Natl Acad Sci USA 94:6414–6419.
21. Liaw L, Almeida M, Hart C E, Schwartz S M, Giachelli C M 1994 Osteopontin promotes vascular cell adhesion and spreading and is chemotactic for smooth muscle cells in vitro. Circ Res 74:214–224.
22. Senger D R, Ledbetter S R, Claffey K P, Papadopoulos-Sergiou A, Perruzzi C A, Detmar M 1996 Stimulation of endothelial cell migration by vascular permeability factor/vascular endothelial growth factor through cooperative mechanisms involving the $\alpha_v\beta_3$ integrin, osteopontin, and thrombin. Am J Pathol 149:293–305.
23. Singh R P, Patarca R, Schwartz J, Singh P, Cantor H 1990 Definition of a specific interaction between the early T lymphocyte activation 1 (ETA-1) protein and murine macrophages in vitro and its effect upon macrophages in vivo. J Exptl Med 171:1931–1942.
24. Weber G F, Ashkar S, Glimcher M J, Cantor H 1996 Receptor-ligand interaction between CD-44 and osteopontin (ETA-1). Science (Wash DC) 271:509–512.
25. Giachelli, C M, Pichler R, Lombardi D, Denhardt D T, Alpers C E, Schwartz S M, Johnson R J 1994 Osteopontin expression in angiotensin II-induced tubulointerstitial nephritis. Kidney Int 45:515–524.
26. Pichler R. Giachelli C M, Lombardi D, Pippin J, Gordon K, Alpers C E, Schwartz S M, Johnson R J 1994 Tubulointerstitial disease in glomerulonephritis. Potential role of osteopontin (uropontin). Am J Path 144:915–926.
27. Diamond J R, Kees-Folts D, Ricardo S D, Pruznak A, Eufemio M 1995 Early and persistent up-regulated expression of renal cortical osteopontin in experimental hydronephrosis. Am J Pathol 146:1455–1466.
28. Lopez C A, Hoyer J R, Wilson P D, Waterhouse P, Denhardt D T 1993 Heterogeneity of osteopontin expression among nephrons in mouse kidney and enhanced expression in sclerotic glomeruli. Lab Invest 69:355–363.
29. Kohri K, Nomura S, Kitamura Y, Nagata T, Yoshioka K, Iguchi T, Yamate T, Umekawa Y, Suzuki H, Sinohara H, Kurita T 1993 Structure and expression of the mRNA encoding urinary stone protein (osteopontin). J Biol Chem 258:15180–15184.
30. McKee M D, Nanci A, Khan S R 1995 Ultrastructural immunodetection of osteopontin and osteocalcin as major matrix components of renal calculi. J Bone Miner Res 10:1913–1929.
31. McKee M D, Nanci A 1996 Osteopontin at mineralized tissue interfaces in bone, teeth, and osseointegrated implants: ultrastructural distribution and implications for mineralized tissue formation, turnover, and repair. Microsc Res Tech 33:141–164.
32. McKee M D, Nanci A 1996 Secretion of osteopontin by macrophages and its accumulation at tissue surfaces during wound healing in mineralized tissues: a potential requirement for macrophage adhesion and phagocytosis. Anat Rec 245:394–409.
33. McKee M D, Nanci A 1996 Osteopontin: An interfacial extracellular matrix protein in mineralized tissues. Connect Tissue Res 35:197–205.
34. Boskey A L, Maresca M, Ullrich W, Doty S B, Butler W T, Prince C W 1993. Osteopontin-hydroxyapatite interactions in vitro: inhibition of hydroxyapatite formation and growth in a gelatin-gel. Bone Miner. 22:147–159.
35. Hunter G K 1996 Interfacial aspects of biomineralization. Curr Opin Solid State Mater Science 1:430–435.
36. Hunter G K, Hauschka P V, Poole A R, Rosenberg L C, Goldberg H A 1996 Nucleation and inhibition of hydroxyapatite formation by mineralized tissue proteins. Biochem J 317:59–64.
37. Craig A M, Denhardt D T 1991 The murine gene encoding secreted phosphoprotein 1 (osteopontin): promoter structure, activity, and induction in vivo by estrogen and progesterone. Gene 100:163–171.
38. Thomas K R, Capecchi M R 1987 Site-directed mutagenesis by gene targeting in mouse embryo-derived stem cells. Cell 51:503–512.
39. Mansour S L, Thomas K R, Capecchi M R 1988 Disruption of the proto-oncogene int-2 in mouse embryo-derived cells: a general strategy for targeting mutations to non-selectable genes. Nature (Lond) 336:348–352.
40. Soriano P, Montgomery C, Geske R, Bradley A 1991 Targeted disruption of the c-src proto-oncogene leads to osteopetrosis in mice. Cell 64:693–702.
41. Prince C W, Oosawa T, Butler W T, Tomana M, Bhown A S, Bhown M, Schrohenloher R E 1987 Isolation, characterization, and biosynthesis of a phosphorylated glycoprotein from rat bone. J Biol Chem 262:2900–2907.
42. Rittling S R, Novick K E 1997 Osteopontin expression in mammary gland development and tumorigenesis. Cell Growth Differn 8:1061–1069.
43. Fisher L W, Hawkins G R, Tuross N, Termine J D 1987 Purification and partial characterization of small proteoglycans I and II, bone sialoproteins I and II, and osteonectin from the mineral compartment of developing human bone. J. Biol. Chem. 262:9702–9708.
44. Bendayan M 1995 Colloidal gold post-embedding immunocytochemistry. Progr. Histochem. Cytochem. 29:1–159.
45. Takahashi N, Akatsu A, Udagawa N. Sasaki T, Yamaguchi A, Moseley J, Martin T J, Suda T 1988 Osteoblastic cells are involved in osteoclast formation. Endocrinology 123:2600–2602.
46. Udagawa N, Takahashi N, Akatsu T, Sasaki T, Yamaguchi A, Kodama H, Martin T J, Suda T 1989 The bone marrow-derived stromal cell lines MC3T3-G2/PA6 and ST2 support osteoclast-like cell differentiation in cocultures with spleen cells. Endocrinology 125:1805–1813.
47. Matsumoto H N, Tamura M, Denhardt D T, Obinata M, Noda M 1995 Establishment and characterization of bone marrow stromal cell lines that support osteoclastogenesis. Endocrinology 136:4084–4091.
48. Franzen A, HeinegArd D 1985 Isolation and characterization of two sialoproteins present only in bone calcified matrix. Biochem J 232:715–724.
49. Akatsu T, Tamura, T, Takahashi N, Udagawa N, Tanaka S, Sasaki T, Yagamushi A, Nagata N, Suda T 1992 Preparation and characterization of a mouse osteoclast-like multinunucleated cell population. J. Bone Min. Res. 7:1297–1306.
50. Grigoriadis A E, Wang Z Q, Cecchini M G, Hofstetter W. Felix R, Fleisch H A, Wagner E F 1994 c-Fos: a key regulator of osteoclast-macrophage lineage determination and bone remodeling. Science (Wash DC) 266:443–448.
51. Butler W T 1995 Structural and functional domains of osteopontin. Ann. N.Y. Acad. Sci. 760:6–11.
52. Brown L F, Berse B, Van de Water L I, Papadopoulos-Sergiou A, Peruzzi C A, Manseau E J, Dvorak H R, Senger D R 1992 Expression and distribution of osteopontin in human tissues; widespread association with luminal epithelial surfaces. Mol. Biol. Cell. 3:1169–1180.
53. Chen J, Singh K, Mukherjee B B, Sodek J 1993 Developmental expression of osteopontin (OPN) mRNA in rat tissues: evidence for a role for OPN in bone formation and resorption. Matrix 13:113–120.
54. Shiraga H, Min W. VanDusen W J, Clayman M D, Miner D, Terrell C H, Sherbotie J R, Foreman J W, Przysiecki C, Neilson E G, Hoyer J R 1992 Inhibition of calcium oxalate crystal growth in vitro by uropontin, a new member of the aspartic-acid rich protein superfamily. Proc Natl Acad Sci USA 89:426–430.
55. Worcester E M, Blumenthal S S, Beshensky A M, Lewand D L 1992 The calcium oxalate crystal growth inhibitor protein produced by mouse kidney cortical cells in culture is osteopontin. J Bone and Min Res 7:1029–1036.

56. Zheng, X, Saunders T L, Camper S A, Samuelson L C, Ginsburg D 1995 Vitronectin is not essential for normal mammalian development and fertility. Proc Natl Acad Sci USA 92:12426–12430.
57. Saga Y, Yagi T, Ikawa Y, Sakakura T. Aizawa S 1992 Mice develop normally without tenascin. Genes Dev 6:1821–1831.
58. Goldberg H A, Hunter G K 1995 The inhibitory activity of osteopontin on hydroxyapatite formation in vitro. Ann NY Acad Sci 760:305–308.
59. Moradian-Oldak J. Frolow F, Addadi L, Weiner S 1992 Interactions between acidic matrix macromolecules and calcium phosphate ester crystals: relevance to carbonate apatite formation in biomineralization. Proc R Soc Lond [Biol] 24:47–55.
60. Aizenberg J, Hanson J, Ilan M, Leiserowitz L, Koetzle T F, Addadi L, Weiner S 1995 Morphogenesis of calcitic sponge spicules: a role for specialized proteins interacting with growing crystals. FASEB J. 9:262–268.
61. Yamate T, Mocharla H, Taguchi Y, Igietseme J U, Manolagas S C, Abe E 1997 Osteopontin expression by osteoclast and osteoblast progenitors in the murine bone marrow: Demonstration of its requirement for osteoclastogenesis and its increase after ovariectomy. Endocrinology 138:3047–3055.
62. Young B A, Burdmann E A, Johnson R J, Alpers C E, Giachelli C M, Eng E, Andoh T, Bennett W M, Couser W G 1995 Cellular proliferation and macrophage influx precede interstitial fibrosis in cyclosporine nephrotoxicity. Kidney Int 48:439–438.
63. Lampe M A, Patarca R, Iregui M V, Cantor H 1991 Polyclonal B-cell activation by the Et-1 cytokine and the development of autoimmune disease. J Immunol 147:2902–2906.
64. Giachelli C M, Lombardi D, Johnson R J, Murry C E, Almeida M. 1998 Evidence for a role of osteopontin in macrophage infiltration in response to pathological stimuli in vivo. Am J Pathol 152: 353–358.
65. McKee M D, Nanci A. 1996 Secretion of osteopontin by macrophages and its accumulation at tissue surfaces during wound healing in mineralized tissues: A potential requirement for macrophage adhesion and phagocytosis. Anat Rec 245:394–409.
66. Rodan G 1995 Osteopontin overview. Ann NY Acad Sci 760:1–5.
67. Sorensen E S, Rasmussen L K, Moller L, Jensen P H, Hojrup P, Petersen T E 1994 Localization of transglutaminase-reactive glutamine residues in bovine osteopontin. Biochem J 304:13–16.
68. Evans et al., (1981) Nature 292:154–156.
69. Bradley et al., (1984) Nature 309:255–258.
70. Gossler et al., (1986) Proc. Natl. Acad. Sci. 83:9065–9069.
71. Frohman et al., (1989) Cell 56:145–147.
72. Bradley et al., (1992) Bio/Technology 10:534–539.
73. Greendale et al., (1993) J. Am. Geriatr. 41:426–436.
74. Fukushima et al., (1991) Anat. Rec. 231:298–315.
75. Crippes et al., (1994) J. Bone Min. Res. 9: S178.
76. Nesbitt et al., (11930 Exp. Cell Res. 195:368–375.
77. Yamamoto et al., (1993) J. Bone. Min. Res. 3:S123.
78. Liaw et al., (1998) J. Clinical Investigation 101:1468–1478.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A transgenic mouse whose germ cells comprise a homozygous null mutation in the endogenous nucleic acid sequence encoding osteopontin, wherein the mutation is created by insertion of a neomycin cassette, in reverse orientation to osteopontin transcription, at a restriction site in exon 6 of the wild-type endogenous nucleic acid sequence encoding osteopontin, and wherein said mutation has been introduced into said mouse by homologous recombination in an embryonic stem cell such that said mouse does not express a functional mouse osteopontin protein.

2. The transgenic mouse of claim 1, wherein said mouse is fertile and transmits said null mutation to its offspring.

3. The transgenic mouse of claim 1, wherein said null mutation has been introduced into an ancestor of said mouse at an embryonic stage following introduction of embryonic stem cells into a blastocyst.

4. A method of screening for potentially therapeutic agents which affect osteopontin activity, comprising:
    a) administering said agent to the transgenic mouse of claim 1; and
    b) assessing said mouse for an alteration in an osteopontin-related physiological process affected by said agent, said process selected from the group consisting of bone remodeling, inhibition of nitric oxide production, renal ischemic damage, ovariectomized induced osteoporosis and osteoclastogenesis.

5. A method for assessing the activity of potentially therapeutic agents useful for the treatment and prevention of osteoporosis, comprising:
    a) providing a pair of the transgenic mice of claim 1;
    b) ovariectomizing said pair of transgenic mice, wherein said ovariectomy induces osteoporosis;
    c) administering said agent to one of said ovariectomized transgenic mice; and
    d) assessing the affect of said agent on ovariectomized-induced osteoporosis in transgenic mouse treated with said agent, compared to the ovariectomized untreated transgenic mouse.

6. A method of screening for potentially therapeutic agents useful for the treatment of renal ischemia, comprising:
    a) providing a pair of the transgenic mice of claim 1;
    b) clamping renal arteries of said transgenic mice to induce ischemia;
    c) administering said agent to one of said transgenic mice of step (b); and
    d) comparing the transgenic mice to assess the affect of said agent by measuring renal damage induced by renal ischemia.

7. The method of claim 6, wherein renal damage is assessed by measuring levels of blood urea nitrogen following reperfusion of said ischemic kidneys.

8. The method of claim 6, wherein renal damage is assessed by measuring levels of creatinine following reperfusion of said ischemic kidneys.

9. The transgenic mouse of claim 1, wherein said restriction site is an EagI site present in exon 6.

* * * * *